(12) United States Patent
Lo et al.

(10) Patent No.: US 8,722,334 B2
(45) Date of Patent: May 13, 2014

(54) ANALYSIS FOR NUCLEIC ACIDS BY DIGITAL PCR

(75) Inventors: Yuk Ming Dennis Lo, Kowloon (HK); Rossa Wai Kwun Chiu, New Territories (HK)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 421 days.

(21) Appl. No.: 12/914,082

(22) Filed: Oct. 28, 2010

(65) Prior Publication Data

US 2011/0183330 A1 Jul. 28, 2011

Related U.S. Application Data

(63) Continuation of application No. 12/184,100, filed on Jul. 31, 2008, now abandoned.

(60) Provisional application No. 60/953,872, filed on Aug. 3, 2007.

(51) Int. Cl.
*C12Q 1/68* (2006.01)
*C12P 19/34* (2006.01)

(52) U.S. Cl.
USPC .......................... 435/6.12; 435/6.1; 435/6.11

(58) Field of Classification Search
None
See application file for complete search history.

(56) References Cited

U.S. PATENT DOCUMENTS

2005/0042639 A1* 2/2005 Knapp et al. ...................... 435/6
2008/0085521 A1 4/2008 Knapp et al.

FOREIGN PATENT DOCUMENTS

EP 1524321 A 4/2005

OTHER PUBLICATIONS

Haff et al., "Multiplex genotyping of PCR products with Mass Tag-labeled primers," Nucleic Acids Research, 1997, vol. 25, No. 18, pp. 3749-3750.*
Zimmermann et al., "Novel Real-Time Quantitative PCR Test for Trisomy 21," Clinical Chemistry, 2002, vol. 48, No. 2, pp. 363-364.*
Gibson et al., "A Novel Method for Real Time Quantative RT-PCR," Genome Research, 1996, vol. 6, pp. 995-1001.*
Chan et al., "Hypermethylated RASSFIA in Maternal Plasma: A Universal Fetal DNA Marker that Improves the Reliability of Noninvasive Prenatal Diagnosis," Clinical Chemistry, 2006, vol. 52, No. 12, pp. 2211-2218.*
Boynton, K. A. et al., "DNA integrity as a potential marker for stool-based detection of colorectal cancer," *Clinical Chemistry, American Association for Clinical Chemistry*, 2003, vol. 49, No. 7, pp. 1058-1065, Washington, DC.
Chan, K. C. Allen, et al., "Size distributions of maternal and fetal DNA in maternal plasma," *Clinical Chemistry, American Association for Clinical Chemistry*, 2004, vol. 50, No. 1, pp. 88-92, Washington, DC.
Dear, Paul H., "One by one: Single molecule tools for genomics," *Briefings in Functional Genomics and Proteomics*, 2003, vol. 1, No. 4, pp. 397-416, Cambridge, UK.
Diehl, Frank, et al., "BEAMing: Single-Molecule PCR on microparticles in water-in-oil emulsions," *Nature Methods*, 2006, vol. 3, No. 7, pp. 551-559.
Diehl, Frank, et al., "Detection and quantification of mutations in the plasma of patients with colorectal tumors", *Proceedings of the National Academy of Sciences of the United States of America*, 2005, vol. 102 No, 45, pp. 16368-16373.
Li Ying, et al., "Size separation of circulatory DNA in maternal plasma permits ready detection of fetal DNA polymorphisms," *Clinical Chemistry*, 2004, vol. 50, No. 6, pp. 1002-1011.
Lo Y. M. Dennis, et al., "Digital PCR for the molecular detection of fetal chromosomal aneuploidy," *Proceedings of the National Academy of Sciences of the United States of America*, 2007, vol. 104, No. 32, pp. 13116-13121.
Lo Y. M. D. et al., "Quantitative Analysis of cell-free Epstein-barr virus DNA in plasma of patients with nasopharyngeal carcinoma," *Cancer Research, American Association for Cancer Research*, 1999, vol. 59, pp. 1188-1191, Baltimore, MD.
Pohl, Gudren, et al., "Principle and applications of digital PCR," *Expert Review of Molecular Diagnostics, Future Drugs*, 2004, vol. 4, No. 1, pp. 41-47, London, GB.
Pugnale, P. et al., "Real-time multiplex PCR assay to quantify hapatitus C virus RNA in peripheral blood mononuclear cells," *Journal of Virological Methods, Elsevier BV*, 2006, vol. 133, No. 2, pp. 195-204, Netherlands.
Wang, Brant et al., "Increased plasma DNA integrity in cancer patients," *Cancer Research*, 2003, vol. 63, No. 14, pp. 3966-3968.
Yoshitomi, K. J. et al., "Detection of Shiga toxin genes stx1, stx2, and the ΣuidA mutation of E. coli 0157: H7/H-using SYBR<(>R) Green 1 in a real-time multiplex PCR," *Molecular and Cellular Probes, Academic Press*, 2006, vol. 20, No. 1, pp. 31-41, London, GB.
Zimmermann et al., "Novel Real-Time Quantative PCR Test for Trisomy 21," Clinical Chemistry, 2002, vol, 48, No. 2, pp. 363-364.
Gibson et al., "A Novel Method for Real Time Quantative RT-PCR," Genome Research, 1996, vol. 6, pp. 995-1001.

* cited by examiner

*Primary Examiner* — Young J Kim
(74) *Attorney, Agent, or Firm* — Kilpatrick Townsend & Stockton LLP

(57) ABSTRACT

The present invention provides a method for analyzing nucleic acids for their lengths and relative abundance in a sample, based on digital amplification of individual template molecules. This invention has many applications, including those in noninvasive prenatal diagnosis, transplantation monitoring, and the detection and monitoring of cancers and virus-associated diseases.

24 Claims, 17 Drawing Sheets

Figure 4
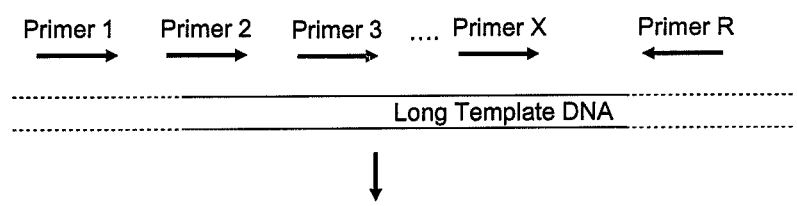
PCR products from Primer 1/Primer R, Primer 2/Primer R,
Primer 3/Primer R to Primer X/Primer R are all present
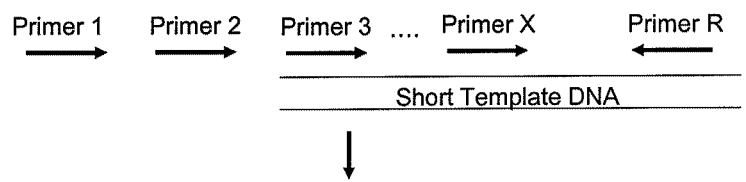
Only PCR products from Primer 3/Primer R....to Primer X/Primer R are present.
No signals from Primer 1/Primer R and Primer 2/Primer R are seen.

Figure 6
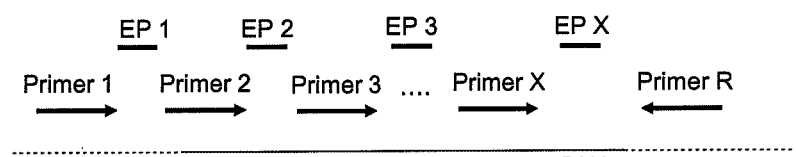
Extension products from EP 1, EP 2, EP 3…..to EP X are all present
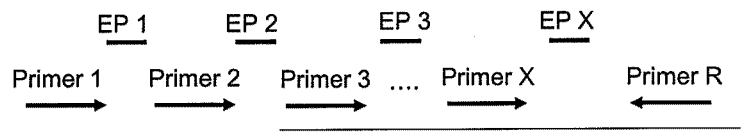
Only extension products from EP 3…..to EP X are present.
No extension products from EP 1 and EP 2.
Key: EP=extension primer

Figure 8

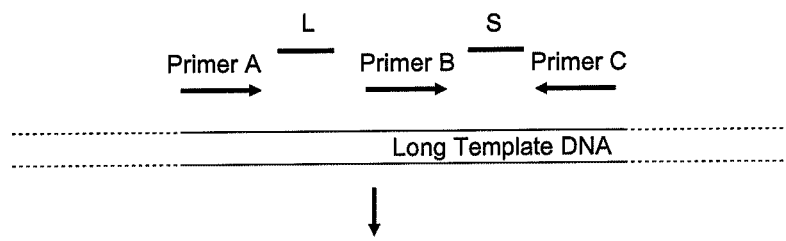

PCR products generated from Primer A/Primer C (213 bp) and Primer B/Primer C (82 bp) are both present. Following the extension reactions, primed by L and S, the L and S extension products are both detectable. The masses of the S extension products for ZFX (X) and ZFY (Y) templateDNA are distinguishable.

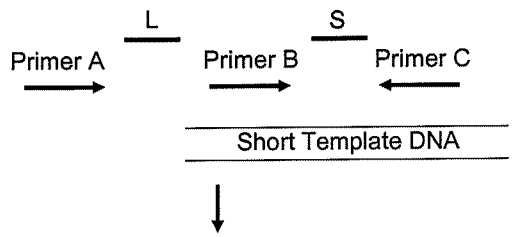

Only PCR product generated from Primer B/Primer C (82 bp) is present. Following the extension reaction, only the S extension products are detectable. The masses of the S extension products for ZFX (X) and ZFY (Y) template DNA are distinguishable.

- ● fractional fetal DNA concentrations (%) measured using all fragments
- ▲ fractional fetal DNA concentrations (%) measured using short fragments only
- ■ percentage of enrichment in fractional fetal DNA concentrations using short fragments only — ● — fractional fetal DNA concentrations (%) measured using all fragments
— ▲ — fractional fetal DNA concentrations (%) measured using short fragments only
— ■ — percentage of enrichment in fractional fetal DNA concentrations using short fragments only —●— fractional fetal DNA concentrations (%) measured using all fragments
—▲— fractional fetal DNA concentrations (%) measured using short fragments only
—■— percentage of enrichment in fractional fetal DNA concentrations using short fragments only ●─ fractional fetal DNA concentrations (%) measured using all fragments
▲─ fractional fetal DNA concentrations (%) measured using short fragments only
■─ percentage of enrichment in fractional fetal DNA concentrations using short fragments only ●— fractional fetal DNA concentrations (%) measured using all fragments
▲— fractional fetal DNA concentrations (%) measured using short fragments only
■— percentage of enrichment in fractional fetal DNA concentrations using short fragments only

SEQUENCE LISTING

<160> NUMBER OF SEQ ID NOS: 32

<210> SEQ ID NO 1
<211> LENGTH: 34
<212> TYPE: DNA
<213> ORGANISM: Artificial Sequence
<220> FEATURE:
<223> OTHER INFORMATION: 213bp-forward PCR primer (Primer A)

<400> SEQUENCE: 1
acgttggatg aactgtgcat aactttgttc ctga                              34

<210> SEQ ID NO 2
<211> LENGTH: 30
<212> TYPE: DNA
<213> ORGANISM: Artificial Sequence
<220> FEATURE:
<223> OTHER INFORMATION: 82bp-forward PCR primer (Primer B)

<400> SEQUENCE: 2
acgttggatg tcattcctga gcaagtgctg                                   30

<210> SEQ ID NO 3
<211> LENGTH: 30
<212> TYPE: DNA
<213> ORGANISM: Artificial Sequence
<220> FEATURE:
<223> OTHER INFORMATION: reverse PCR primer (Primer C)

<400> SEQUENCE: 3
acgttggatg gctaaaacat catctgggac                                   30

<210> SEQ ID NO 4
<211> LENGTH: 20
<212> TYPE: DNA
<213> ORGANISM: Artificial Sequence
<220> FEATURE:
<223> OTHER INFORMATION: 213bp-extension primer (L)

<400> SEQUENCE: 4
aacatcttgg attacaactg                                              20

<210> SEQ ID NO 5
<211> LENGTH: 17

```
<212> TYPE: DNA
<213> ORGANISM: Artificial Sequence
<220> FEATURE:
<223> OTHER INFORMATION: 82bp-extension primer (S)

<400> SEQUENCE: 5
tcatctggga ctgtgca                                                      17

<210> SEQ ID NO 6
<211> LENGTH: 22
<212> TYPE: DNA
<213> ORGANISM: Artificial Sequence
<220> FEATURE:
<223> OTHER INFORMATION: beta-globin gene real-time PCR primer

<400> SEQUENCE: 6
gtgcacctga ctcctgagga ga                                                22

<210> SEQ ID NO 7
<211> LENGTH: 21
<212> TYPE: DNA
<213> ORGANISM: Artificial Sequence
<220> FEATURE:
<223> OTHER INFORMATION: beta-globin gene real-time PCR primer

<400> SEQUENCE: 7
ccttgatacc aacctgccca g                                                 21

<210> SEQ ID NO 8
<211> LENGTH: 26
<212> TYPE: DNA
<213> ORGANISM: Artificial Sequence
<220> FEATURE:
<223> OTHER INFORMATION: beta-globin gene real-time PCR probe
<220> FEATURE:
<221> NAME/KEY: modified_base
<222> LOCATION: (1)...(1)
<223> OTHER INFORMATION: a modified by VIC fluorescent reporter
<220> FEATURE:
<221> NAME/KEY: modified_base
<222> LOCATION: (26)...(26)
<223> OTHER INFORMATION: g modified by 6-carboxytetramethylrhodamine
      (TAMRA)

<400> SEQUENCE: 8
aaggtgaacg tggatgaagt tggtgg                                            26

<210> SEQ ID NO 9
<211> LENGTH: 30
<212> TYPE: DNA
<213> ORGANISM: Artificial Sequence
<220> FEATURE:
<223> OTHER INFORMATION: SERPINB5  (maspin) Mpn_Forward L forward PCR
      primer

<400> SEQUENCE: 9
cgtgtctgag aaatttgtag tgttactatc                                        30

<210> SEQ ID NO 10
<211> LENGTH: 16
<212> TYPE: DNA
<213> ORGANISM: Artificial Sequence
<220> FEATURE:
<223> OTHER INFORMATION: SERPINB5  (maspin) Mpn_Forward S forward PCR
      primer

<400> SEQUENCE: 10
cggtcctgcg tgggcc                                                       16
```

-continued

```
<210> SEQ ID NO 11
<211> LENGTH: 25
<212> TYPE: DNA
<213> ORGANISM: Artificial Sequence
<220> FEATURE:
<223> OTHER INFORMATION: SERPINB5 (maspin) Mpn_Reverse PCR common
      reverse primer

<400> SEQUENCE: 11
gctgtgagtt acatgcatac gtaca                                           25

<210> SEQ ID NO 12
<211> LENGTH: 20
<212> TYPE: DNA
<213> ORGANISM: Artificial Sequence
<220> FEATURE:
<223> OTHER INFORMATION: SERPINB5 (maspin) long PCR product Mpn_Probe L
      probe
<220> FEATURE:
<221> NAME/KEY: modified_base
<222> LOCATION: (1)...(1)
<223> OTHER INFORMATION: c modified by VIC fluorescent reporter
<220> FEATURE:
<221> NAME/KEY: modified_base
<222> LOCATION: (20)...(20)
<223> OTHER INFORMATION: c modified by minor groove binder (MGB)

<400> SEQUENCE: 12
cacattactt ttatttcatc                                                 20

<210> SEQ ID NO 13
<211> LENGTH: 15
<212> TYPE: DNA
<213> ORGANISM: Artificial Sequence
<220> FEATURE:
<223> OTHER INFORMATION: SERPINB5 (maspin) short PCR product Mpn_Probe
      S probe
<220> FEATURE:
<221> NAME/KEY: modified_base
<222> LOCATION: (1)...(1)
<223> OTHER INFORMATION: t modified by 6FAM fluorescent reporter
<220> FEATURE:
<221> NAME/KEY: modified_base
<222> LOCATION: (15)...(15)
<223> OTHER INFORMATION: t modified by minor groove binder (MGB)

<400> SEQUENCE: 13
ttgccgtacg catgt                                                      15

<210> SEQ ID NO 14
<211> LENGTH: 34
<212> TYPE: DNA
<213> ORGANISM: Artificial Sequence
<220> FEATURE:
<223> OTHER INFORMATION: ZFX and ZFY gene region long amplicon F-213bp
      forward digital PCR primer

<400> SEQUENCE: 14
acgttggatg aactgtgcat aactttgttc ctga                                 34

<210> SEQ ID NO 15
<211> LENGTH: 31
<212> TYPE: DNA
<213> ORGANISM: Artificial Sequence
<220> FEATURE:
<223> OTHER INFORMATION: ZFX and ZFY gene region long amplicon F-179bp
      forward digital PCR primer

<400> SEQUENCE: 15
acgttggatg tcagttgtaa tccaagatgt t                                    31
```

```
<210> SEQ ID NO 16
<211> LENGTH: 25
<212> TYPE: DNA
<213> ORGANISM: Artificial Sequence
<220> FEATURE:
<223> OTHER INFORMATION: ZFX and ZFY gene region long amplicon F-149bp
      forward digital PCR primer

<400> SEQUENCE: 16
acgttggatg tttaaggagc tgatg                                      25

<210> SEQ ID NO 17
<211> LENGTH: 30
<212> TYPE: DNA
<213> ORGANISM: Artificial Sequence
<220> FEATURE:
<223> OTHER INFORMATION: ZFX and ZFY gene region short amplicon F-82bp
      forward digital PCR primer

<400> SEQUENCE: 17
acgttggatg tcattcctga gcaagtgctg                                 30

<210> SEQ ID NO 18
<211> LENGTH: 32
<212> TYPE: DNA
<213> ORGANISM: Artificial Sequence
<220> FEATURE:
<223> OTHER INFORMATION: ZFX and ZFY gene region short amplicon F-64bp
      forward digital PCR primer

<400> SEQUENCE: 18
acgttggatg tggactcaga tgtaactgaa ga                              32

<210> SEQ ID NO 19
<211> LENGTH: 27
<212> TYPE: DNA
<213> ORGANISM: Artificial Sequence
<220> FEATURE:
<223> OTHER INFORMATION: ZFX and ZFY gene region short amplicon F-60bp
      forward digital PCR primer

<400> SEQUENCE: 19
acgttggatg gacataactg tgcataa                                    27

<210> SEQ ID NO 20
<211> LENGTH: 29
<212> TYPE: DNA
<213> ORGANISM: Artificial Sequence
<220> FEATURE:
<223> OTHER INFORMATION: ZFX and ZFY gene region short amplicon F-51bp
      forward digital PCR primer

<400> SEQUENCE: 20
acgttggatg aactgaagaa gtttctttA                                  29

<210> SEQ ID NO 21
<211> LENGTH: 30
<212> TYPE: DNA
<213> ORGANISM: Artificial Sequence
<220> FEATURE:
<223> OTHER INFORMATION: ZFX and ZFY gene region R-a reverse PCR primer

<400> SEQUENCE: 21
acgttggatg gctaaaacat catctgggac                                 30

<210> SEQ ID NO 22
```

```
<211> LENGTH: 31
<212> TYPE: DNA
<213> ORGANISM: Artificial Sequence
<220> FEATURE:
<223> OTHER INFORMATION: ZFX and ZFY gene region R-b reverse PCR primer

<400> SEQUENCE: 22
acgttggatg aacatcttgg attacaactg a                               31

<210> SEQ ID NO 23
<211> LENGTH: 20
<212> TYPE: DNA
<213> ORGANISM: Artificial Sequence
<220> FEATURE:
<223> OTHER INFORMATION: ZFX and ZFY gene region long amplicon L-a
      extension primer

<400> SEQUENCE: 23
aacatcttgg attacaactg                                            20

<210> SEQ ID NO 24
<211> LENGTH: 19
<212> TYPE: DNA
<213> ORGANISM: Artificial Sequence
<220> FEATURE:
<223> OTHER INFORMATION: ZFX and ZFY gene region long amplicon L-b
      extension primer

<400> SEQUENCE: 24
catcattcct gagcaagtg                                             19

<210> SEQ ID NO 25
<211> LENGTH: 18
<212> TYPE: DNA
<213> ORGANISM: Artificial Sequence
<220> FEATURE:
<223> OTHER INFORMATION: ZFX and ZFY gene region long amplicon L-c
      extension primer

<400> SEQUENCE: 25
cacacatgga tggtgatc                                              18

<210> SEQ ID NO 26
<211> LENGTH: 17
<212> TYPE: DNA
<213> ORGANISM: Artificial Sequence
<220> FEATURE:
<223> OTHER INFORMATION: ZFX and ZFY gene region short amplicon S-a
      extension primer

<400> SEQUENCE: 26
tcatctggga ctgtgca                                               17

<210> SEQ ID NO 27
<211> LENGTH: 17
<212> TYPE: DNA
<213> ORGANISM: Artificial Sequence
<220> FEATURE:
<223> OTHER INFORMATION: ZFX and ZFY gene region short amplicon S-b
      extension primer

<400> SEQUENCE: 27
gttcctgatg acccaga                                               17

<210> SEQ ID NO 28
<211> LENGTH: 30
<212> TYPE: DNA
<213> ORGANISM: Artificial Sequence
```

```
<220> FEATURE:
<223> OTHER INFORMATION: PLAC4 polymorphic SNP (rs8130833) long amplicon
      forward duplex PCR primer

<400> SEQUENCE: 28
acgttggatg gcctggaagt aacgtgatcc                                          30

<210> SEQ ID NO 29
<211> LENGTH: 30
<212> TYPE: DNA
<213> ORGANISM: Artificial Sequence
<220> FEATURE:
<223> OTHER INFORMATION: PLAC4 polymorphic SNP (rs8130833) short
      amplicon forward duplex PCR primer

<400> SEQUENCE: 29
acgttggatg tagaaccatg tttaggccag                                          30

<210> SEQ ID NO 30
<211> LENGTH: 31
<212> TYPE: DNA
<213> ORGANISM: Artificial Sequence
<220> FEATURE:
<223> OTHER INFORMATION: PLAC4 polymorphic SNP (rs8130833) reverse
      duplex PCR primer

<400> SEQUENCE: 30
acgttggatg gcaacaccat ttgggttaaa t                                        31

<210> SEQ ID NO 31
<211> LENGTH: 20
<212> TYPE: DNA
<213> ORGANISM: Artificial Sequence
<220> FEATURE:
<223> OTHER INFORMATION: PLAC4 polymorphic SNP (rs8130833) long amplicon
      extension primer

<400> SEQUENCE: 31
agtatagagc cataaaagcc                                                     20

<210> SEQ ID NO 32
<211> LENGTH: 18
<212> TYPE: DNA
<213> ORGANISM: Artificial Sequence
<220> FEATURE:
<223> OTHER INFORMATION: PLAC4 polymorphic SNP (rs8130833) short
      amplicon extension primer

<400> SEQUENCE: 32
aggccagata tattcgtc                                                       18
```

ANALYSIS FOR NUCLEIC ACIDS BY DIGITAL PCR

CROSS-REFERENCES TO RELATED APPLICATIONS

This application is a continuation of U.S. application Ser. No. 12/184,100, filed Jul. 31, 2008 which claims priority to U.S. Provisional Patent Application No. 60/953,872, filed Aug. 3, 2007, the disclosure of which is incorporated by reference in its entirety.

BACKGROUND OF THE INVENTION

The analysis of the size of nucleic acids is useful for many research and diagnostic applications. Electrophoresis, e.g., agarose gel electrophoresis, polyacrylamide gel electrophoresis and capillary electrophoresis, is commonly used for the size analysis of nucleic acids. Mass spectrometry has also been used for size analysis, as nucleic acid fragments of different sizes, such as those produced by a primer extension reaction, have different molecular masses (Ding and Cantor, 2003, *Proc Natl Acad Sci USA*, 100, 7449-7453).

Below are several examples of the use of size analysis. For example, the presence of a mutation which creates a restriction enzyme site can be detected by treatment with the said enzyme, followed by the analysis of the sizes of the treated products. The presence of shorter fragments of a particular size indicates that the mutation is present. Conversely, the presence of longer DNA fragments corresponding to the unrestricted state is suggestive of the absence of the mutation. If the restriction enzyme used is sensitive to the methylation status of the target DNA fragment, then this type of analysis can also be used for the analysis of DNA methylation. Thus, if an enzyme that only cuts unmethylated DNA is used, then the presence of shorter restricted DNA fragments is indicative of the presence of unmethylated DNA. Conversely, the presence of the longer unrestricted DNA fragments is suggestive of the presence of methylated DNA. The interpretation of these results would be reversed if an enzyme such as McrBC (Sutherland, et al. 1992, *J Mol Biol*, 225, 327-348), which cuts methylated DNA and which does not cut unmethylated DNA, is used.

As another example, it is known that cell-free fetal DNA in maternal plasma is of a smaller size than maternal DNA (Chan, et al. 2004, *Clin Chem*, 50, 88-92; Li, et al. 2004, *Clin Chem*, 50, 1002-1011) (see also European Patent Application No. 03405742.2 "Non-invasive detection of fetal genetic traits"). Thus, size fractionation by electrophoresis has been used to enrich for fetal DNA in maternal plasma (Li, et al. 2005, *JAMA*, 293, 843-849).

In the field of oncology, increased DNA integrity has been observed in cancer patients (Hanley, et al. 2006, *Clin Cancer Res*, 12, 4569-4574; Jiang, et al. 2006, *Int J Cancer*, 119, 2673-2676; Umetani, et al. 2006, *J Clin Oncol*, 24, 4270-4276; Wang, et al. 2003, *Cancer Res*, 63, 3966-3968) (see also U.S. Pat. No. 6,964,846). This phenomenon is thought to be related to necrotic changes which are associated with the tumor. DNA integrity in cancer patients has been analyzed by separate real-time PCR assays for different sized amplicons. Exact Sciences also has a proprietary DNA integrity assay (for more information see the web site exactsciences.com/applied/applied.html).

DNA size analysis has also been used for the analysis of viral-derived nucleic acid sequences, such as the size of Epstein-Barr virus (EBV) DNA in the plasma of patients with nasopharyngeal carcinoma and certain lymphomas (Chan, et al. 2003, *Cancer Res*, 63, 2028-2032). Size analysis has also been used for the measurement of RNA integrity (Wong, et al. 2006, *Clin Cancer Res*, 12, 2512-2516; Wong, et al. 2005, *Clin Chem*, 51, 1786-1795). Such analysis might be of use in clinical diagnosis, as decreased RNA integrity has been observed in cancer patients. Also, placental RNA in the plasma of pregnant women has been shown to be consisted of partially degraded fragments, with a 5' preponderance (Wong, et al. 2005, *Clin Chem*, 51, 1786-1795). It has been suggested that oxidative stress would decrease the integrity of such placental-derived mRNA (Rusterholz, et al. 2007, *Fetal Diagn Ther*, 22, 313-317). Digital PCR followed by DNA sequencing has been used for the analysis of the size distribution of plasma DNA in patients with colorectal tumors (Diehl, et al. 2005, *Proc Natl Acad Sci USA*, 102, 16368-16373).

The present invention provides novel methods for analyzing the size of nucleic acids, especially nucleic acids derived from the same longer sequence, and the relative abundance of such nucleic acids of different lengths in a test sample.

BRIEF SUMMARY OF THE INVENTION

The present invention provides a new method for analyzing target nucleic acids in a sample. Target nucleic acids can be any nucleic acids of varying lengths originated from the same source, for instance, the same gene or the same chromosomal region, although the target nucleic acids may originate from one individual, or from multiple individuals (e.g., a sample from a pregnant woman may contain nucleic acids from her and her fetus; or, a sample from a transplant recipient may contain nucleic acids from the recipient and the donor), or from more than one type of cells (e.g. tumor cells, placental cells, blood cells). This method comprises the following steps: first, multiple equal (or identical) fractions are prepared from the sample. Among these equal fractions, at least 50% of the fractions contain no more than one target nucleic acid molecule in each one of the fractions. In some cases, these multiple fractions are directly taken from the sample in equal amount; in other cases, these multiple fractions are obtained, also in equal amount, from a dilution, or less commonly a concentration, that is first made from a portion or the entirety of the sample. In some embodiments, the first step of the claimed method is performed by a microfluidics system. In other embodiments, the fractions can be prepared by binding the target onto a solid surface, e.g., the prelude to a bridge amplification system (website is www.promega.com/geneticidproc/ussymp7proc/0726.html).

In some embodiments, the sample to be analyzed is from a pregnant woman, for instance, the sample may be blood, plasma, serum, saliva, or a cervical lavage sample. In some cases, each of the target nucleic acids includes at least a portion of chromosome 13, 18, 21, X, or Y; or each of the target nucleic acids may include a genetic polymorphism (e.g., single nucleotide polymorphism (SNP)); or each of the target nucleic acids may include at least a portion of a gene linked to a disease (e.g., the β-globin gene in β-thalassemia or the cystic fibrosis transmembrane conductance regulator gene in cystic fibrosis) or a genetic polymorphism linked to such a gene (e.g., the SNPs rs713040, rs10768683 and rs7480526 within the β-globin gene locus).

In other embodiments, the sample to be analyzed is from a cancer patient. For instance, the sample may be blood, plasma, serum, saliva, or tumor tissue. In some cases, each of the target nucleic acids comprises at least a portion of the KRAS, erbB-2, p16, RASSF1A gene sequence; or each of the target nucleic acids is from a virus genome, such as the genome of Epstein Barr Virus (EBV), Human Papilloma Virus (HPV), or Hepatitis B Virus (HBV).

Second, identical amplification reactions are carried out in each and every one of the multiple equal fractions. In every fraction, at least three different oligonucleotide primers are used: at least one forward primer combined with at least two reverse primers, or at least two forward primers combined with at least one reverse primer. Each of the forward or reverse primers has a distinct and definitive nucleotide sequence, designed such that each forward/reverse primer pair permits the amplification of different regions of the target nucleic acid sequence, producing amplification products (i.e., amplicons) in distinct lengths. In some embodiments, the amplification reaction is a polymerase chain reaction (PCR) or a variation of a PCR, such as emulsion PCR, real-time PCR, reverse transcription PCR (RT-PCR), or real-time RT-PCR, or PCR conducted on a solid surface, e.g., bridge amplification system (website is www.promega.com/geneticidproc/ussymp7proc/0726.html). For RT-PCR, there is a prior step of reverse transcription that produces a DNA sequence from a target RNA sequence originally present in the sample, and the DNA sequence then can be amplified. In some cases, a fluorescent dye, such as SYBR Green or LC Green, is present in the PCR.

When performing the amplification reactions in the second step of the claimed method, various primers can be added to the reaction mix either at the same time or at separate times. In other words, different forward/reverse primer sets may be present in the reaction all at once, permitting all possible amplicons to be produced concurrently; or the reaction may start with at least one primer set and later have one or more primers added to provide additional primer set(s), allowing the initial and additional amplification reactions to take place in a consecutive manner.

In the third step, the polynucleotide sequence or sequences that have been produced by the amplification reaction(s) (i.e., amplicons) within each one of the multiple equal fractions of the sample are detected and distinguished from each other, based on from which forward/reverse primer set the amplicons have been amplified. Various means are available for the detection step, such as melting curve analysis, electrophoresis, flow cytometry, or sequence-specific hybridization with probes attached to detectable labels, each probe having a distinct detectable label and specifically hybridizing with an amplified nucleotide sequence from a pair of forward and reverse primers. In some cases, the detectable labels are distinct fluorescent molecules. In other cases, the third step of the claimed method is performed by primer extension reactions, using a distinct oligonucleotide primer to initiate a polymerization process for each distinct amplicon. The products of the primer extension reactions are detected by mass spectrometry or by electrophoresis. In some embodiments, the second and third steps are performed by BEAMing.

In the fourth step, the number of fractions are counted in separate categories according to the presence of various amplicons. As an example, one forward primer (A) and two reverse primers (a and b) are used in the amplification reaction. If fraction #1 is positive for amplicon Aa, which is the amplification product from forward primer A and reverse primer a, and also positive for amplicon Ab, which is the amplification product from forward primer A and reverse primer b, fraction #1 will be counted once in the category of $Aa^+/Ab^+$. On the other hand, if fraction #2 is positive for amplicon Aa but not Ab, then it will score one count in the category of $Aa^+/Ab^-$. All negative reactions need not be counted as their number can be deducted from the total number of fractions and the number of fractions containing at least one amplicon.

BRIEF DESCRIPTION OF THE DRAWINGS

FIGS. 1-12 depict various schemes of primer design and means for detecting different polynucleotide sequences following amplification reactions involving distinct primer sets.

DEFINITIONS

Figure 1:
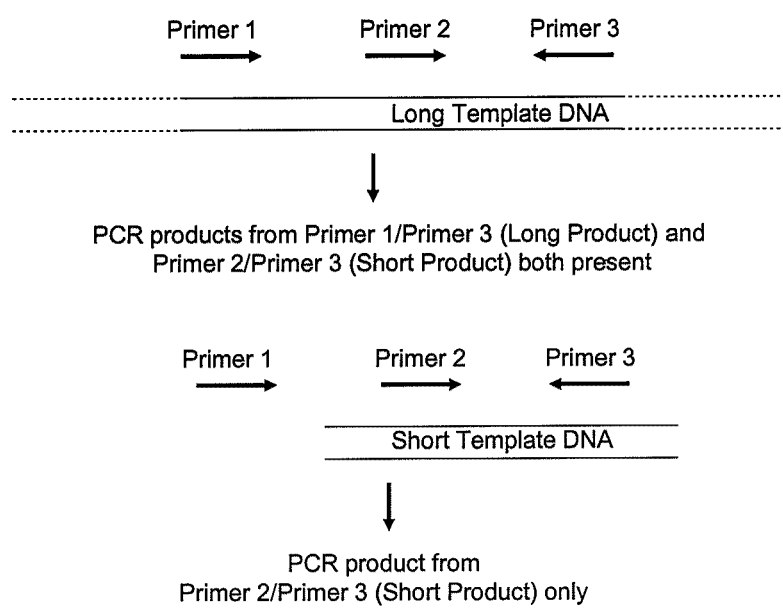

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term "oligonucleotide" as used herein is generally interchangeable with the term "polynucleotide," although a polynucleotide sequence of relatively shorter length (e.g., no more than 50 nucleotides, preferably no more than 30 nucleotides, and more preferably no more than 15-20 nucleotides) is frequently referred to as an "oligonucleotide."

The term "gene" refers to a segment of genomic DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, "target nucleic acids" being analyzed in a sample are a collection of nucleic acid molecules of the same origin (e.g., from the same chromosome, genomic locus, or gene, although the molecules may come from one individual, or multiple individuals, or more than one type of cells, such as tumor cells, placental cells, blood cells, etc.) but in different lengths. For instance, segments of β-globin coding sequence maybe present in a test sample as "target nucleic acid molecules" of varying lengths. Because each of these target nucleic acids contains at least a portion of the β-globin gene, primers having sequences corresponding (or complementary) to various locations within the β-globin gene can then be used for target nucleic acid length analysis by the claimed method. Whereas nucleic acids of varying lengths derived from the same origin, e.g., the same gene, are collectively referred to as "target nucleic acids," the term "1 (one) target nucleic acid molecule" is used to referred to any one member of the target nucleic acids collection, regardless of its length or actual sequence.

A "nucleotide sequence-specific hybridization" as used herein refers to a means for detecting the presence and/or quantity of a polynucleotide sequence based on its ability to form Watson-Crick base-pairing, under appropriate hybridization conditions, with a polynucleotide or oligonucleotide probe of a known sequence. Examples of such hybridization methods include Southern blotting and Northern blotting.

"Primers" as used herein refer to oligonucleotides that can be used in an amplification method, such as a polymerase chain reaction (PCR), to amplify a predetermined target nucleotide sequence. In a typical PCR, at least one set of primers, one forward primer and one reverse primer, are needed to amplify a target polynucleotide sequence. Conventionally, when a target DNA sequence consisting of a (+) strand and a (−) strand is amplified, a forward primer is an oligonucleotide that can hybridize to the 3' end of the (−) strand under the reaction condition and can therefore initiate the polymerization of a new (+) strand; whereas a reverse primer is an oligonucleotide that can hybridize to the 3' end of the (+) strand under the reaction condition and can therefore initiate the polymerization of a new (−) strand. As an example, a forward primer may have the same sequence as the 5' end of the (+) strand, and a reverse primer may have the same sequence as the 5' end of the (−) strand.

The method of the present invention involves amplification reactions using multiple sets of forward and reverse primers. These amplification reactions may take place at the same time or different times. For instance, an amplification reaction may take place "concurrently" with other amplification reaction(s) when one or more sets of primers are present in the same reaction mixture at the same time. On the other hand, amplification reactions may take place "consecutively" when at least one set of primers is made complete at a different time in the reaction mixture, so that the amplification using this particular primer set takes place at a time different from that of the other amplification reaction(s).

As used in this application, a "microfluidics system" refers to a system, typically an automated system, that can manipulate very small volume of fluid samples with required precision. A "microfluidics system" suitable for this invention is capable of accurately taking one or more aliquots from a fluid sample and distributing the aliquots into separate, individually defined compartments (e.g., individual wells on a plate). The volume of each aliquot is generally in the range of nanoliters ($10^{-9}$ liter) to picoliters ($10^{-12}$ liter).

As used in this application, an "emulsion polymerase chain reaction" refers to a polymerase chain reaction in which the reaction mixture, an aqueous solution, is added into a large volume of a second liquid phase that is water-insoluble, e.g., oil, and emulsified prior to the amplification process, so that droplets of the reaction mixture act as micro-reactors and therefore achieve a higher concentration for a target nucleic acid in at least some of the micro-reactors.

As used in this application, "BEAMing" (beads, emulsions, amplification, and magnetics) refers to a modified emulsion PCR process. At least one of the PCR primers is conjugated with a molecule that is a partner of a known binding pair. For instance, a biotin moiety may be conjugated to a forward primer used in the PCR. In each reaction compartment, one or more metal beads coated with the other member of the binding pair, e.g., streptavidin, are provided. Upon completion of the amplification step, the amplicon from the labeled primer is adsorbed to the coated bead(s), which in turn can be concentrated and isolated by magnetic beads. For more description of BEAMing, see, e.g., Diehl et al., *Nat. Methods.* 2006 July; 3(7):551-9.

As used in this application, a "melting curve analysis" refers to an analysis in which the melting point of a double-stranded DNA is determined by way of measuring changes in a detectable signal indicative of the transition from double-stranded state to single-stranded state of the DNA molecule. Typically, a fluorescent dye that binds only double stranded DNA by intercalation between the base pairs and therefore does not bind single stranded DNA is used in the assay, such as ethidium bromide or SYBR Green. The assay is carried out by gradually increasing the temperature of a mixture of DNA and a labeling material (e.g., SYBR Green) while monitoring the level of the label signal. When the DNA strands separate or "melt," a quick and significant change in the signal output occurs. The melting point temperature can thus be determined. Because the melting point of a double-stranded DNA molecule is determined by factors including length, nucleotide sequence, and how well two strands match, this assay can be used for discriminating DNA molecules of different lengths and sequences.

A "PCR on a solid phase" is a type of polymerase chain reaction that yields amplification products immobilized on a solid surface or support. "Bridge amplification" is an example. It is a technology that uses primers bound to a solid phase for the extension and amplification of solution phase target nucleic acid sequences. The name refers to the fact that during the annealing step, the extension product from one bound primer forms a bridge to the other bound primer. All amplified products are covalently bound to the surface, and can be detected and quantified without electrophoresis. In one study, bridge systems were developed to amplify and detect single nucleotide sequence polymorphisms. Primers carrying 5'-amines were covalently attached to silica, polymethylmethacrylate, or polystyrene bead supports and used in place of solution phase primers under standard PCR reaction conditions. Amplification reactions were monitored by the incorporation of $^{32}$P-labeled deoxynucleotide triphosphates into support-bound form. The presence of the correct product was confirmed by restriction analysis of the solid phase products. In another variation of this theme, the amplification reactions are detected by hybridization with one or more fluorescent probes labeled with one or more types of fluorescent reporters.

DETAILED DESCRIPTION OF THE INVENTION

This invention provides a method for the quantitative measurement of nucleic acid molecules of different sizes by the use of single molecule analysis. Thus, a sample containing nucleic acids is diluted or fractionated to an extent such that many of the test wells will not contain any target nucleic acid molecule. For wells containing the target nucleic acid molecules, most of them will just contain a single one. The nucleic acid molecules contained in the reaction wells will then be amplified by a nested series of primers amplifying target sequences of different sizes, such as a series of polymerase chain reactions (PCR) utilizing several sets of forward and reverse primers. Following amplification, wells containing a long nucleic acid template will contain the longest amplicon plus all of the smaller ones. A well containing a shorter nucleic acid template will produce one or more amplicons, up to the size delineated by the template molecule. Thus, by counting the number of wells containing each combination of amplicons, a determination of the size distribution of nucleic acid molecules in the original sample can be achieved.

One configuration of this analysis is indicated in the diagram of FIG. 1. This configuration consists of 3 PCR primers: Primer 1, Primer 2 and Primer 3. Primer 1 and Primer 3 will form a long PCR product. Primer 2 and Primer 3 will form a short PCR product. The sizes of the long and short PCR products can be changed from application to application. In one version of this, the long product can be 200 bp while the short product can be 80 bp. The long product can also for example be 100 bp, 150 bp, 250 bp, 300 bp, 350 bp or 450 bp. The short product can be 70 bp, 60 bp, 50 bp, 40 bp, 30 bp or 25 bp in length. Different combinations of sizes of the long and short products are possible and would be used for different applications. Thus, the three primers will be used simultaneously to amplify the diluted or fractionated nucleic acid sample mentioned to above in a digital fashion (Vogelstein and Kinzler, 1999, *Proc Natl Acad Sci USA*, 96, 9236-9241) (see also U.S. Pat. Nos. 6,440,706, 6,753,147, and US Patent Application Publication Nos. 20050130176, 20060046258 (especially section 0040) and 20040096892).

The present invention is different from that of Diehl et al. (*Proc Natl Acad Sci USA*, 102, 16368-16373, 2005), who used digital PCR followed by DNA sequence to determine the size of plasma DNA fragment in separate PCRs but did not obtain or analyze multiple amplicons of different sizes present in one single amplification reaction.

The method of this invention can be used for both DNA and RNA targets, with DNA polymerase being directly used for DNA targets. With RNA targets, a reverse transcription step will need to be first performed. Thus, RNA targets can be amplified by either a reverse transcription step followed by a DNA amplification step using different enzymes, or to use an enzyme, such as the *Thermus thermophilus* (Tth) polymerase that possesses both reverse transcriptase and DNA polymerase functions (Myers and Gelfand 1991, *Biochemistry*, 30, 7661-7666).

If a well contains a nucleic acid fragment that is long and contains the sequence between Primer 1 and Primer 3, then it would have both the PCR products from Primer 1/Primer 3 and Primer 2/Primer 3. On the other hand, if a well contains a short nucleic acid fragment containing just the sequence encompasses Primer 2 and Primer 3, then only the PCR product from Primer 2/Primer 3 will be formed.

To detect which product(s) has (have) been formed in each well, a number of methods can be used. One example is to use agarose gel or capillary electrophoresis. Another method is to add a fluorescent dye, e.g., SYBR Green or LC Green, which would bind to double stranded DNA and then to perform melting curve analysis (Ririe, et al. 1997, *Anal Biochem*, 245, 154-160; Wittwer, et al. 2003, *Clin Chem*, 49, 853-860). Melting curve analysis can be used to discriminate the products produced by Primer 1/Primer 3 and by Primer 2/Primer 3.

Figure 2:
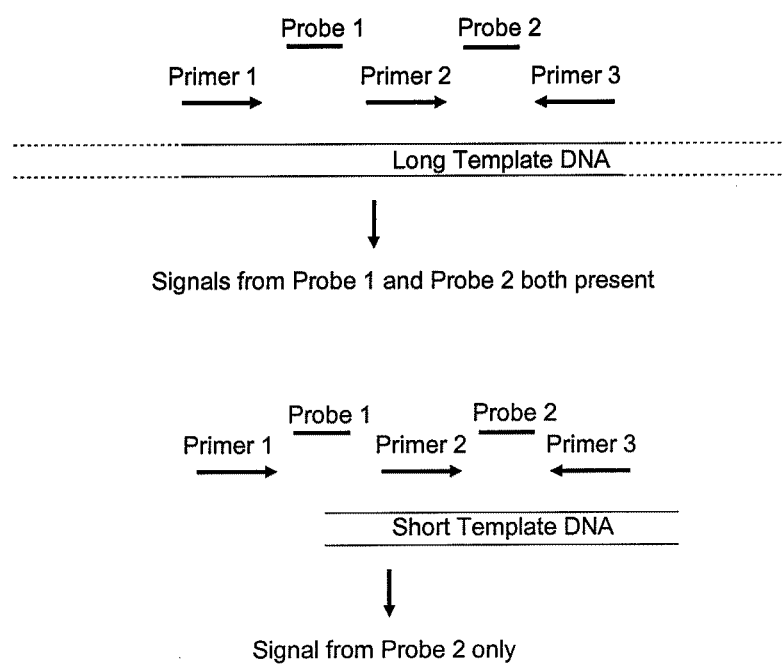

Yet another method is to add two fluorescent probes to the system, as illustrated in FIG. 2. The two probes in this scheme, labeled with different fluorescent reporters, can be TaqMan probes, molecular beacons, or other probes well-known to those in the art for performing real-time PCR (Heid, et al. 1996, *Genome Res*, 6, 986-994; Lo, et al. 1998, *Am J Hum Genet*, 62, 768-775). Thus, a well containing a nucleic acid fragment at least as long as that delineated by Primer 1 and Primer 3 will produce the long PCR product (produced by Primer 1/Primer 3) and will contain fluorescence signals from both Probe 1 and Probe 2. On the other hand, a well containing a nucleic acid fragment at least as long as that delineated by Primer 2 and Primer 3, but shorter than that delineated by Primer 1 and Primer 3, will generate the short PCR product (produced by Primer 2/Primer 3) and will contain only the fluorescence signal from Probe 2. Such real-time digital PCR analysis can be performed in any of the machines well-known to those in the art, such as an Applied Biosystems 7900 Sequence Detector, or a real-time PCR system with a microfluidics chip, e.g., the Fluidigm BioMark System (Warren, et al. 2006, *Proc Natl Acad Sci USA*, 103, 17807-17812), or the OpenArray Technology of BioTrove (website www.biotrove.com/technologies/thru/, and Morrison, et al., 2006, *Nucleic Acids Res* 34: e123).

Figure 3:
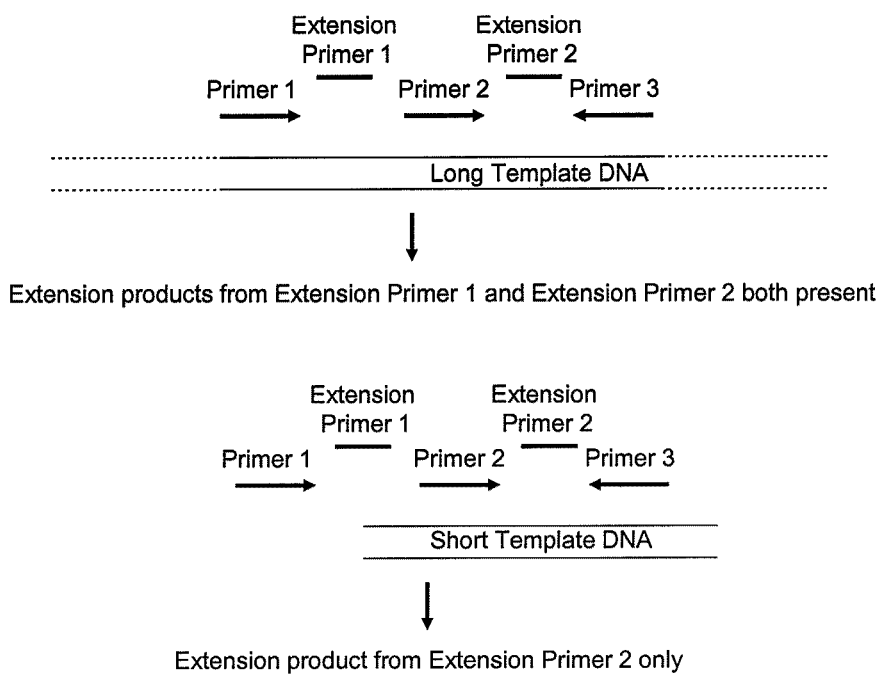

Another method for scoring the wells is illustrated in FIG. 3. For this configuration, the digital PCR is first conducted using Primer 1, Primer 2 and Primer 3. After that the amplification products from each well are then subjected to a primer extension reaction using Extension Primer 1 and Extension Primer 2, such as using the homogenous MassEXTEND assay from Sequenom (Ding and Cantor 2003, *Proc Natl Acad Sci USA*, 100, 7449-7453). For the extension reaction, dideoxynucleotide triphosphate with or without deoxynucleotide triphosphate is used. In one configuration, Extension Primer 1 and Extension Primer 2 will both be extended if the long PCR product (produced by Primer 1/Primer 2) is present. In this configuration, only Extension Primer 2 will be extended if only the short PCR product (produced by Primer 2/Primer 3) is present. The extension products from each well will then be analyzed such as using matrix-assisted laser desorption/ionization time-of-flight mass spectrometry (Ding and Cantor 2003, *Proc Natl Acad Sci USA*, 100, 7449-7453). Extension Primer 1 and Extension Primer 2 are designed in such a way that the extended versions of these primers are easily distinguishable on the mass spectrometer. In other embodiments, the extension primers can be replaced with sequencing primers, with the respective amplicons distinguished by sequencing reactions.

The above configurations are for illustrative purposes only, using the scenario of measuring the amount of nucleic acid fragments of two different sizes. However, this method can be used for measuring the concentration of nucleic acid fragments of 3 or more size categories. FIG. 4 illustrates this general concept. In this configuration, multiple forward primers are used: Primer 1, Primer 2, Primer 3 . . . to Primer X. One reverse primer, Primer R, is used. If we have a piece of template nucleic acid which is longer than the largest amplicon, namely, that delineated by Primer 1/Primer R, then all PCR products will be produced. However, template nucleic acids which are shorter than that will only produce a subset of the amplicons, namely, those shorter than or equal to the length of the template. By counting the number of wells with each of these various types of PCR product combinations, the size distribution of the original nucleic acid sample can be determined.

Figure 5:
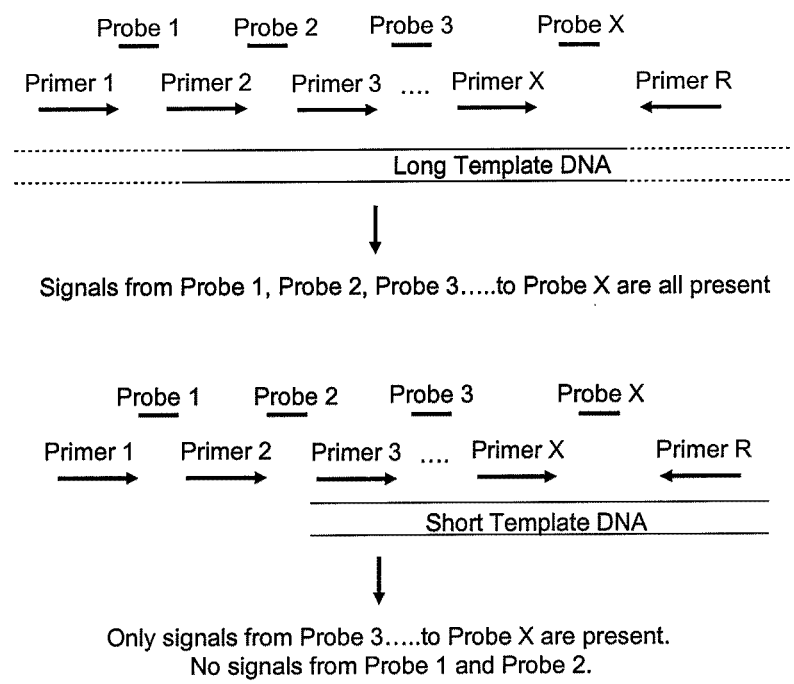

The detection of the PCR products in this multiple primer configuration (i.e., Primers 1 to X, and Primer R) can be performed with the use of fluorescent probes, each labeled with a different fluorescence reporter or combinations of fluorescence reporters. See FIG. 5.

Multiple primer extension assays can also be used to detect these multiple PCR products, such as using the homogenous MassEXTEND assay from Sequenom (Ding and Cantor 2003, *Proc Natl Acad Sci USA*, 100, 7449-7453). For the extension reaction, dideoxynucleotide triphosphate with or without deoxynucleotide triphosphate is used. In one configuration, all of the extension primers will be extended if the long PCR product (produced by Primer 1/Primer R) is present (see diagram below). In this configuration, with progressively shorter template nucleic acid, only the extension primers targeting the respectively PCR products will be extended. The extension products from each well will then be analyzed using either electrophoresis OR by using mass spectrometry, e.g., matrix-assisted laser desorption/ionization time-of-flight mass spectrometry (Ding and Cantor 2003, *Proc Natl Acad Sci USA*, 100, 7449-7453). The extension primers are designed in such a way that their extension products are easily distinguishable on the mass spectrometer or electrophoresis. This scheme is illustrated in FIG. 6. In other embodiments, the extension primers can be replaced with sequencing primers, with the respective amplicons distinguished by sequencing reactions.

Figure 7:
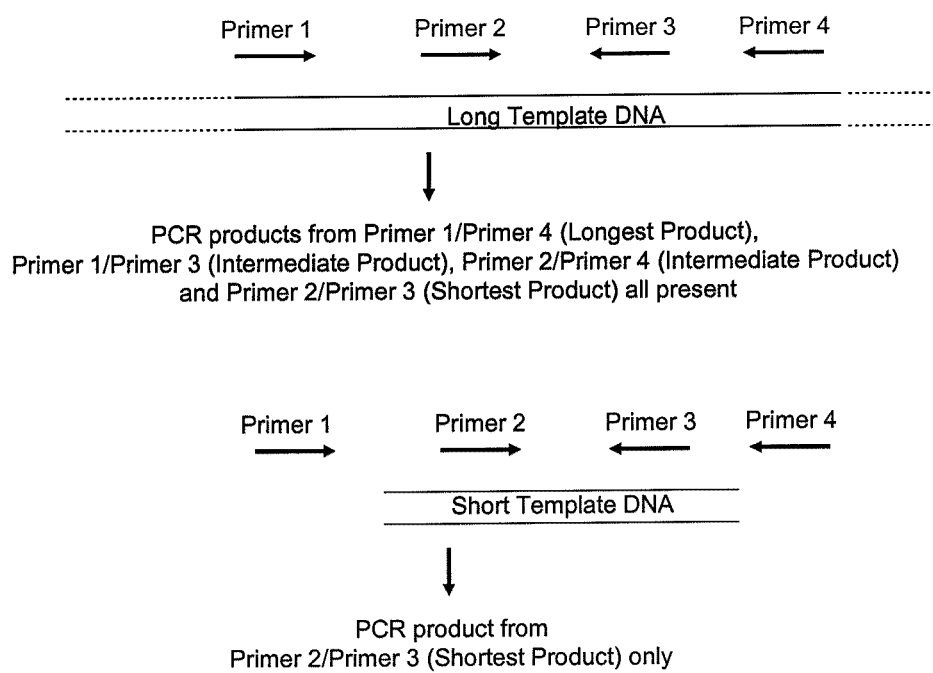

In all of the above configurations, we have illustrated the principle of this invention with the use of two or more primers in one orientation; and only a single primer in the reverse orientation. However, it is also possible to practice this invention using more than one primer in the reverse orientation. One such configuration is illustrated in FIG. 7. One advantage of having multiple primers in both orientations is that for a given number of primers, the number of possible PCR products, and thus the size categories, is higher than in the scenario when only one primer is used in the reverse orientation. For example, with a total of 4 primers, in which 2 are in one orientation and 2 are in the reverse orientation (as illustrated above), 4 size categories are possible (one longest, one shortest and two intermediate categories (which can be of different sizes)). On the other hand, if 3 primers are in one orientation and only one is in the reverse orientation, then only 3 size categories would be possible.

Similar to the configurations involving a single primer in the reverse orientation, for configurations in which more than one primer are used in both orientations, the detection of the various PCR products can be performed by electrophoresis, fluorescence probes and primer extension followed by mass spectrometry. Furthermore, other variants of digital PCR can be performed in the fashion described in this invention, including: nanoliter PCR microplate systems (Morrison, et al. 2006, *Nucleic Acids Res*, 34, e123), emulsion PCR (Dressman, et al. 2003, *Proc Natl Acad Sci USA*, 100, 8817-8822), and polony PCR (Mitra and Church 1999, *Nucleic Acids Res*, 27, e34).

EXAMPLES

The following examples are provided by way of illustration only and not by way of limitation. Those of skill in the art will readily recognize a variety of non-critical parameters that could be changed or modified to yield essentially the same or similar results.

Example 1

DNA Size Analysis in Buffy Coat Sample and Plasma

This example illustrates the use of the present invention for comparing the size of DNA in buffy coat and plasma. Plasma DNA are short in nature as previously reported (Chan et al., supra) while buffy coat DNA is genomic DNA and thus is expected to be longer than plasma DNA. Two plasma samples and one buffy coat sample were obtained from male subjects. These DNA samples should have both X and Y chromosomal sequences. In this example, the ZFX and ZFY genes were targeted. The PCR primers and extension primers have the sequences as tabulated below (SEQ ID NOS:1-5):

Primer Sequences:

| | |
|---|---|
| 213bp-forward PCR primer (Primer A) | 5'-ACGTTGGATGAACTGTGCATAAC TTTGTTCCTGA-3' |
| 82bp-forward PCR primer (Primer B) | 5'-ACGTTGGATGTCATTCCTGAGCA AGTGCTG-3' |
| Reverse PCR primer (Primer C) | 5'-ACGTTGGATGGCTAAAACATCAT CTGGGAC-3' |
| 213bp-extension primer (L) | 5'-AACATCTTGGATTACAACTG-3' |
| 82bp-extension primer (S) | 5'-TCATCTGGGACTGTGCA-3' |

ZFX and ZFY are homologous genes and therefore are co-amplifiable by the same primers. In our assay, the two genes are distinguished by the extension products of the S extension primer. The configuration of this assay is illustrated in FIG. 8.

The buffy coat DNA sample and the two plasma DNA samples were diluted to single molecule level. The amount of DNA corresponding to one template per well was determined by serially diluting the DNA samples and testing with the real-time PCR assay for the β-globin gene in a 96-well format. The reaction was set up using 2× TaqMan Universal PCR Master Mix (Applied Biosystems) in a reaction volume of 5 μL. 300 nM of each primer and 200 nM of the probe were used in each reaction. The primer sequences were 5'-GTGCAC-CTGACTCCTGAGGAGA-3' (SEQ ID NO:6) and 5'-CCT-TGATACCAACCTGCCCAG-3' (SEQ ID NO:7) and the probe sequence was 5'-(VIC)AAGGTGAACGTGGAT-GAAGTTGGTGG(TAMRA)-3' (SEQ ID NO:8), where TAMRA is 6-carboxytetramethylrhodamine. The reaction was carried out in an ABI PRISM 7900HT Sequence Detection System (Applied Biosystems) with the reaction condition of 50° C. for 2 min, 95° C. for 10 min, followed by 50 cycles 95° C for 15 s and 60° C. for 1 min.

The size of the template DNA was determined by digital PCR. DNA was amplified in a 5-uL PCR reaction. Each reaction contained 1.25× HotStar Taq PCR buffer with 1.875 mM MgCl$_2$ (Qiagen), an additional 1.625 mM MgCl$_2$ (Qiagen), 50 μM each of dATP, dGTP, and dCTP, 100 μM dUTP (Applied Biosystems), 100 nM each of the forward primers for the 213 bp- and the 82 bp-amplicon (Integrated DNA Technologies), 200 nM of the reverse primer, and 0.1 U of HotStar Taq Polymerase (Qiagen). The PCR reaction was initiated at 95° C. for 15 min, followed by 94° C. for 20 s, 55° C. for 30 s, and 72° C. for 1 min for 50 cycles, and a final incubation at 72° C. for 3 min. 384 digital PCRs were carried out for the buffy coat sample and 192 digital PCRs were carried out for each of the plasma DNA sample.

PCR products were subjected to shrimp alkaline phosphatase treatment with 0.12 μL of shrimp alkaline phosphatase (Sequenom), 0.068 μL of MassARRAY™ Homogenous MassEXTEND™ (hME) buffer (Sequenom), and 0.612 μL of water. The mixture was incubated at 37° C. for 40 min followed by 85° C. for 5 min. hME assays were then performed. Each reaction contained 463 nM of the extension primer for the 213 bp-amplicon, 771 nM of the extension primer for the 82 bp-amplicon, 1.15 U of Thermosequenase (Sequenom), and 64 μM each of ddATP, ddCTP, ddTTP, and dGTP (Sequenom). The reaction conditions were 94° C. for 2 min, followed by 94° C. for 5 s, 52° C. for 5 s, and 72° C. for 5 s for 80 cycles.

The results are tabulated below. L denotes the presence of the extension products by the extension primer L, indicating the presence of a long PCR product of 213 bp. X and Y denote the presence of the X and Y extension products, respectively, from extension primer S. Thus, if either X or Y signal is present alone, then it would indicate the presence of template DNA shorter than or equal to 82 bp. On the contrary, the presence of the L extension product should be accompanied by either an X or a Y signal, denoted as LX or LY in the table. If just an L signal is present, then it would mean that either the short PCR by Primer B/Primer C or the extension reaction by S has failed. As indicated in the table, this has not happened for any of the wells.

|  | Total Well Number | Number of Wells with No Signals | L | X | Y | LX | LY | LXY |
|---|---|---|---|---|---|---|---|---|
| Buffy coat DNA | 384 | 235 | 0 | 1 | 5 | 62 | 60 | 21 |
| Plasma DNA 1 | 192 | 112 | 0 | 22 | 30 | 5 | 11 | 4 |
| Plasma DNA 2 | 192 | 131 | 0 | 19 | 19 | 10 | 8 | 2 |

The above data have shown that the buffy coat sample contained predominantly DNA molecules at least as long as 213 bp, as most of the wells had either a LX or LY combination of signals. Only 6 wells contained either the short X or Y signal. The 21 LXY wells indicate that these wells contain more than one molecule, at least one of which was a long one (either a long X or a long Y molecule).

Conversely, the two plasma samples contained predominantly sequences shorter than 213 bp, as evidenced by the preponderance of X only and Y only signals.

Example 2

Size Analysis of DNA in the Plasma of Pregnant Women by Digital PCR

DNA in the plasma of a pregnant woman is predominantly derived from maternal cells, with a small proportion being derived from the fetus (Lo, et al. 1998, *Am J Hum Genet*, 62, 768-775). When studying the total DNA as a whole, the DNA in the plasma of pregnant women is larger than that in the plasma of non-pregnant women (Chan, et al. 2004, *Clin Chem*, 50, 88-92). On the other hand, when one compares the fetal-derived and maternal-derived DNA in maternal plasma, then the fetal-derived DNA is generally of a smaller size than that derived from the mother (Chan, et al. 2004, supra).

Size analysis by the digital PCR-based approach described here allows one to measure the relative concentrations of DNA of different sizes in maternal plasma. The principle of this approach is illustrated by using the model system in which a pregnant woman is carrying a male fetus. The fetal DNA contains X and Y chromosomal sequences; while the maternal DNA contains X, but not Y, chromosomal sequences. The ZFX gene is used as a marker of the X chromosome; while the ZFY gene is used as a marker of the Y chromosome. The configuration of this system is exactly the same as that described in Example 1. The detection of the long and short PCR products is carried out by primer extension followed by mass spectrometry. The short PCR products can be further classified into those that are derived from the X and those that are derived from the Y chromosome. The primer extension products of the X- and Y-derived products can be distinguished by their masses.

As described in Example 1, different types of signals can be expected from this digital PCR system. Thus, the presence of L, the extension product of the long PCR product, is indicative of the presence of template DNA as least as long as the sequence delineated by Primer A and Primer C (or at least as long as the sequence amplifiable by Primer A and Primer C, which can be slightly shorter than that delineated by the two primers). The presence of L in a particular well will be expected to be accompanied by either X or Y or both (if there is more than one molecule in a particular well). On the other hand, if a well contains either the signal of X or Y, but no L, then this is indicative of the presence of template molecule that is shorter than the sequence delineated by Primer A and Primer C, but longer than that delineated by Primer B and Primer C.

As fetal DNA is enriched in the shorter DNA fragments, the proportion of wells positive for a Y (i.e., fetal) signal but without the L signal is expected to be higher than the corresponding proportion of wells positive for both the Y and L signals. In other words, this invention will allow one to selectively focus on a subset of wells containing template molecules of a particular size.

To illustrate the above concepts, an experiment was carried out using this system on a maternal plasma sample. The results are tabulated below:

|  | Total Well Number | Number of Wells with No Signals | L | X | Y | LX | LY | LXY |
|---|---|---|---|---|---|---|---|---|
| M2891P | 384 | 197 | 0 | 97 | 16 | 65 | 1 | 5 |

As can be seen, most of the Y chromosome-containing (i.e., fetal DNA) wells contained short template DNA, as evidenced by the fact that they contained the Y signal indicative of short DNA, but not the LY signal combination indicative of long DNA. The relatively large number of wells containing the LX signal combination mainly contained DNA derived from the pregnant women (i.e., non-fetal DNA). As an illustration of the usefulness of size analysis by digital PCR, for case M2891P, without the size analysis, 22 of the 384 wells (i.e., 5.7%) contained Y-specific (i.e., fetal) signals. On the other hand, when one looks at the wells containing short template DNA (i.e., those with either the X or the Y signals; but no L signal), the proportion of wells with Y-specific signals increased to 16/(16+97), i.e., 14.1%.

This method has the advantage that one can easily change the size window of interest. For example, further increase in the wells showing a fetal-specific signal can be achieved by further reducing the size of short PCR, e.g., to 60 bp, to 50 bp, or to 40 bp and below. Similarly, one can also readily change the size of the long PCR to between 150 bp and 200 bp; or to between 100 bp and 149 bp.

This approach has considerable advantage over those previously reported, such as electrophoresis (Li, et al. 2004, *Clin Chem*, 50, 1002-1011), as the electrophoresis step as well as the post-electrophoresis harvesting of the DNA are potentially contamination-prone.

The method of the present invention can work in a synergistic manner with existing methods for enhancing the fractional concentrations of fetal DNA in maternal plasma, e.g., electrophoresis (Li, et al. 2004, *Clin Chem*, 50, 1002-1011) and the use of formaldehyde or other additives in suppressing the concentration of maternal-derived DNA in maternal plasma (Dhallan, et al. 2004, *JAMA*, 291, 1114-1119).

Example 3

Methylation Analysis by Methylation-sensitive Restriction Enzyme Treatment

Some restriction enzymes will cleave or not cleave their target sequences dependent on the DNA methylation status at or around the target sequence. Most methylation-sensitive restriction enzymes will cut an unmethylated sequence but will not cut a methylated sequence. There is also a relative small subset of enzymes, such as McrBC which will cut methylated sequences, leaving unmethylated sequences intact (Sutherland, et al. 1992, *J Mol Biol*, 225, 327-348).

In either case, the restricted DNA fragment will be shorter than the uncut template. Thus, the present invention can be used to obtained quantitative information regarding the cut and uncut DNA molecules.

In this example, the gene SERPINB5 coding for maspin is used as an example (Dokras, et al. 2002, *Placenta*, 23, 274-280). SERPINB5 is hypomethylated in the placenta and hypermethylated in the blood cells of pregnant women (Chim, et al. 2005, *Proc Natl Acad Sci USA*, 102, 14753-14758).

Figure 9:
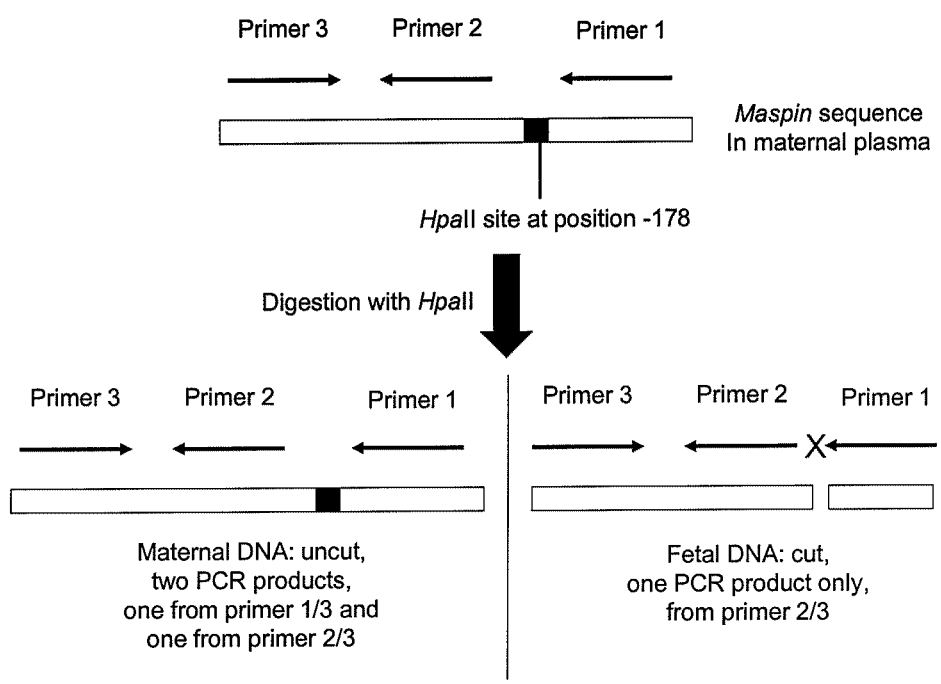

In the scheme shown in FIG. 9, two forward primers (primer 1 and primer 2) and one reverse primer are designed. One of the forward primers (primer 1) is upstream of a restriction site for a methylation-sensitive restriction enzyme, such as the HpaII site at position −178 of the SERPINB5 gene. When plasma DNA is cut by the methylation-sensitive restriction enzyme, such as HpaII as illustrated in the diagram, the maternal blood cell DNA, which is hypermethylated, will be uncut. On the other hand, for fetal (placental) DNA which is hypomethylated, the site will be cut by HpaII. For digital PCR analysis of maternal plasma DNA using this strategy, maternal plasma DNA will be extracted as described (Lo, et al. 1998, *Am J Hum Genet*, 62, 768-775), then the plasma DNA will be digested with HpaII. The HpaII-treated plasma DNA will then be quantified by real-time PCR using primer 2 and primer 3, plus a TaqMan probe in between the two primers. Then, the HpaII-treated plasma DNA will be diluted such that for the subsequent digital PCR analysis, on average each reaction well will only contain one SERPINB5 molecule which could be amplified using primer 2 and primer 3. Then, the diluted HpaII-treated plasma DNA will be subjected to digital PCR analysis using the combination of primer 1, primer 2 and primer 3. Two TaqMan or hybridization probes will also be added, one targeting a sequence between primer 2 and primer 3, and the other one straddling the HpaII restriction site between primer 1 and primer 2. The two probes will be labeled with different fluorescent reporters, e.g., FAM for one and VIC for the other. If a well contains a molecule containing the maternal SERPINB5 sequence, then signals from both probes will be present. On the other hand, if a well contains a molecule containing the fetal SERPINB5 sequence, then only the signal from the probe between primer 2 and primer 3 will be present. Thus, the counting of the number of wells containing the fetal pattern of signals will allow us to count the number of fetal SERPINB5 molecules.

To illustrate the practical utility of the above concepts, the following example was realized in the laboratory.

Assay design. The long and short SERPINB5 assays involve the use of two forward primers (Mpn_Forward L and Mpn_Forward S) and one common reverse primer (Mpn_Reverse). The detection of the long and short PCR products depends on the probes Mpn_Probe L and Mpn_Probe S, respectively. A methylation-sensitive restriction endonuclease digestion site is located between Mpn_Probe L and Mpn_Forward S. As a result, both PCR products would be expected to be detectable in mock-digested DNA samples. With the addition of the restriction enzyme, the detection of the long signal would be expected to decrease for the hypomethylated DNA samples. The sequences for the primers and probes are listed as below (SEQ ID NOS:9-13):

Primers and Probes Sequences

| | |
|---|---|
| Mpn_Forward 1 | 5'-CGTGTCTGAGAAATTTGTAGTGTTACACTATC-3' |
| Mpn_Forward S | 5'-CGGTCCTGCGTGGGCC-3' |
| Mpn_Reverse | 5'-GCTGTGAGTTACATGCATACGTACA-3' |
| Mpn_Probe L | 5'-VIC-CACATTACTTTTATTTCATC(MGB)-3' |
| Mpn_Probe S | 5'-6FAM-TTGCCGTACGCATGT(MGB)-3' |

Methylation-sensitive restriction enzyme digestion. The methylation-sensitive restriction endonuclease, HpaII (New England Biolabs), was used to digest the maternal blood cell DNA and the placental DNA samples at 37° C. for 16 hours in a 20 μL, reaction mixture. 100 μg of each DNA sample was digested with 20 U of the HpaII enzyme. A mock-digested aliquot was included for each sample. For mock-digestion, an equal amount of DNA was subjected to the same digestion condition without the addition of enzyme.

Real-time PCR on the 7900 platform. The long and short SERPINB5 assays were performed as duplex on the mock-digested and HpaII-digested DNA samples from two pairs of maternal blood cells and placentas. Each 5 μL real-time PCR included 1× TaqMan® Universal PCR Master Mix (Applied Biosystems), 62.5 nM each of the TaqMan® probe L and probe S (Applied Biosystems), 900 nM each of the forward primer L (Integrated DNA Technologies) and the common reverse primer (Integrated DNA Technologies), and 450 nM forward primer S (Integrated DNA Technologies). A total of 32 replicates were performed for each sample at an input of 6.25 pg DNA per reaction. The thermal profile was 50° C. for 2 min, 95° C. for 10 min, followed by 50 cycles of 95° C. for 15 s, and 60° C. for 1 min.

Real-time PCR on the Fluidigm platform. Digital PCR for the SERPINB5 promoter sequence was performed on the mock-digested and HpaII-digested DNA samples from one pair of maternal blood cell and placenta. For each panel (equivalent to 765 reaction wells), 1× TaqMan® Universal PCR Master Mix (Applied Biosystems), 31.25 nM each of the TaqMan® probe L and probe S (Applied Biosystems), 900 nM each of the forward primer L (Integrated DNA Technologies) and the common reverse primer (Integrated DNA Technologies), and 450 nM forward primer S (Integrated DNA Technologies) were mixed together with 3.5 ng of DNA sample. The thermal profile was 50° C. for 2 min, 95° C. for 10 min, followed by 40 cycles of 95° C. for 15 s, and 58° C. for 1 min.

Results

Real-time PCR on the 7900 platform. Detection of the long and short SERPINB5 molecules was at similar levels for the maternal blood cell DNA with and without enzyme digestion. The level of detectable long DNA molecules after enzyme digestion decreases for the two placenta samples, while the level of short DNA remained similar with and without enzyme digestion.

|  | Total well number | Mock digestion | | HpaII digestion | |
|---|---|---|---|---|---|
|  |  | Long | Short | Long | Short |
| Maternal blood cell 1 | 32 | 25 | 25 | 28 | 29 |
| Maternal blood cell 2 | 32 | 16 | 27 | 23 | 29 |
| Placenta 1 | 32 | 18 | 24 | 6 | 19 |
| Placenta 2 | 32 | 22 | 25 | 8 | 30 |

Real-time PCR on the Fluidigm platform. Detection of the long and short SERPINB5 molecules was at similar levels for maternal blood cell DNA with and without enzyme digestion. The number of detectable long DNA molecules after enzyme digestion decreases for the placenta sample, while the number of short DNA remained similar with and without enzyme digestion.

|  | Total well number | Mock digestion | | HpaII digestion | |
|---|---|---|---|---|---|
|  |  | Long | Short | Long | Short |
| Maternal blood cell | 765 | 351 | 358 | 330 | 339 |
| Placenta | 765 | 262 | 269 | 99 | 275 |

Using this principle, one can also develop a system for detecting fetal DNA molecules which bear an opposite methylation state to that of SERPINB5. One of such DNA target is the RASSF1A gene which is hypermethylated in the placenta but hypomethylated in maternal blood cells (Chan, et al. 2006, *Clin Chem,* 52, 2211-2218; Chiu, et al. 2007, *Am J Pathol,* 170, 941-950), namely for the counting of fetal-derived RASSF1A sequence in maternal plasma. Following cutting with a restriction enzyme which cuts the unmethylated maternal RASSF1A while leaving the fetal sequence intact, the restriction products can be analyzed using the digital PCR-based size analysis system described in this invention. The fetal pattern in this case would be given by the presence of a two probe signals in a particular well.

It will be obvious to those of skill in the art that a multiplex PCR system combining both the SERPINB5 and RASSF1A systems would be possible, with the four fluorescent probes each labeled using a different reporter. Alternatively, the SERPINB5 and RASSF1A systems could be separately applied in different digital PCR analyses. In either scenario, the number of wells positive for just fetal-derived SERPINB5 sequences will be compared to the number of wells positive for just fetal-derived RASSF1A sequences. The ratio, or difference in these numbers will give an indication as to whether the fetus has trisomy 18. An increased ratio of these numbers (SERPINB5/RASSF1A) is indicative of trisomy 18. Sequential Probability Ratio Test (Zhou et al. 2001, *Nat Biotechnol,* 19, 78-81; Zhou, et al. 2002, *Lancet,* 359, 219-225) or other statistical procedures well-known to those of skill in the art can be used to provide statistical evidence for the confidence with which a diagnosis of trisomy 18 can be made.

The scheme outlined in FIG. 9 can be used for detecting other fetal-specific sequence in maternal plasma, as long as an enzyme cleavage site (such as those for methylation-sensitive restriction enzyme; but other enzymes can also be used) can be found which can differentiate fetal from maternal nucleic acids.

Apart from detecting the different PCR products using fluorescent probes, it is also possible to use primer extension reactions, followed by mass spectrometry, as illustrated in Examples 1 and 2.

Example 4

Detection of Fetal Chromosomal Aneuploidy from Maternal Plasma

In a separate study, we have recently demonstrated the feasibility of using digital relative chromosome dosage (RCD) for detecting the presence of aneuploid DNA in a mixture of aneuploid and euploid DNA (Lo Y M D, Lun F M F, Chan K C A, Tsui N B Y, Chong K C, Lau T K, Leung T Y, Zee B C Y, Cantor C R, Chiu R W K. Digital PCR for the molecular detection of fetal chromosomal aneuploidy. *Proc. Natl. Acad. Sci. U.S.A.* 104:13116-13121, 2007). One example of aneuploid DNA is that obtained from a subject with trisomy 21 (Down syndrome). One example of a mixture of aneuploidy and euploid DNA is maternal plasma DNA obtained from a pregnant woman carrying a fetus with trisomy 21.

For digital RCD analysis, the higher the proportion of fetal DNA, the smaller the number of digital PCR assays that would be needed to detect the presence of aneuploid DNA. Hence, the use of the present invention would allow us to focus on a subpopulation of DNA molecules in maternal plasma of a particular size range, in which the fractional concentration of fetal-derived DNA molecules is higher than that in the total DNA in maternal plasma.

Figure 10:
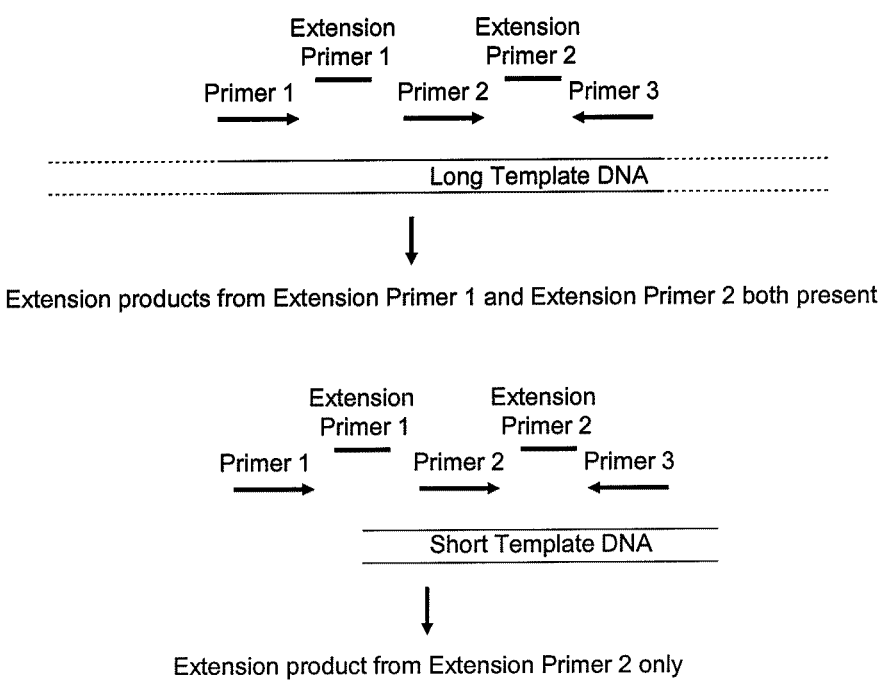

As an illustration of the use of the present invention for the detection of fetal chromosomal aneuploidy from maternal plasma, the design depicted in FIG. 10 is used. Primer 1, Primer 2, and Primer 3 targets paralogous loci (Deutsch, et al. 2004, *J Med Genet,* 41, 908-915), such as a pair of loci located on chromosome 21 and chromosome 1. In the latter example, the loci on chromosome 21 and chromosome 1 have significant homology to one another, with differences in a relatively small number of nucleotides. Thus, Primer 1, Primer 2 and Primer 3 are designed such that the two paralogs have virtually identical sequences. The two primer pairs: (1) Primer 1/Primer 3 (long PCR product) and (2) Primer 2/Primer 3 (short PCR product) would both amplify the chromosome 21 and chromosome 1 paralogs. Extension Primer 1 is designed such that it would bind to and extend the Primer 1/Primer 3 PCR product from either paralog. It is not essential that the extension products of Extension Primer 1 from each paralog be distinguishable from each other. Extension Primer 2 is designed to bind to the PCR product of both paralogs. The target site of Extension Primer 2 is designed such that following extension, the extension products from the chromosome 21 and chromosome 1 paralogs are distinguishable from one another.

The first step of the analysis is the dilution of the sample DNA to an extent such that most reaction wells would be amplifying either no or just a single template molecule. Then, PCR amplification using Primer 1, Primer 2 and Primer 3 is carried out. Then, mass extension reaction using Extension Primer 1 and Extension Primer 2 is carried out. The extension products, if any, from each well are then analyzed by mass spectrometry, such as using matrix-assisted laser desorption/ionization mass spectrometry (Ding and Cantor 2003, *Proc Natl Acad Sci USA,* 100, 7449-7453). The mass spectra from each well will inform us what template molecule it contains prior to amplification. Thus, any well showing the extension product of Extension Primer 1 indicates that it contains a template DNA molecule of a length as least as long as that delineated by Primer 1 and Primer 3. A well containing the Extension Primer 1 product would also be expected to contain the extension product of Extension Primer 2.

Conversely any well containing just the extension product, if any, Extension Primer 2; but not the extension product from Extension Primer 1 indicates that it contain a short DNA template. A short DNA template is one which is at least as long as the sequence delineated by Primer 2 and Primer 3, but shorter than the sequence delineated by Primer 1 and Primer 3. The mass of the extension product of Extension Primer 2 would indicate whether the product is derived from the chromosome 21 or the chromosome 1 paralog.

As fetal DNA in maternal plasma is relatively shorter than the maternally-derived counterpart (Chan, et al. 2004, Clin Chem, 50, 88-92), for noninvasive prenatal diagnosis of fetal trisomy 21, it would be advantageous to focus the analysis on the subset of wells showing just the Extension Primer 2 products, but no Extension Primer 1 products. The proportion of such wells containing fetal-derived template DNA would be higher than if all wells are considered, without consideration to the results of such size analysis. This focused subset of wells can be further subdivided into those showing a chromosome 21 signal and those showing a chromosome 1 signal. If the fetus has trisomy 21, then the number of wells showing a chromosome 21 signal should be overrepresented in comparison with that of wells showing a chromosome 1 signal. Statistical evidence of such overrepresentation can be obtained by a number of methods, including the Sequential Probability Ratio Test (SPRT) (Zhou, et al. 2001, Nat Biotechnol, 19, 78-81; Zhou, et al. 2002, Lancet, 359, 219-225; Lo Y M D, Lun F M F, Chan K C A, Tsui N B Y, Chong K C, Lau T K, Leung T Y, Zee B C Y, Cantor C R, Chiu R W K. Digital PCR for the molecular detection of fetal chromosomal aneuploidy. Proc. Natl. Acad. Sci. U.S.A. 104:13116-13121, 2007), the false-discovery rate (El Karoui, et al. 2006, Stat Med, 25, 3124-3133), etc.

The above example of using paralogous sequences as targets is only described by way of example, and not as limitation of the present invention. This present invention can be practiced using separate primers and extension primers for the chromosome 21 and the reference chromosome. In this configuration, three primers each will be used for chromosome 21 and the reference chromosome. Indeed more than three primers can be used, for covering a range of sizes for digital analysis. Furthermore, this approach can be used to detect other chromosome aneuploidies, besides trisomy 21, by targeting the chromosome involved in the aneuploidy concerned, e.g., chromosome 18 in trisomy 18, chromosome 13 in trisomy 13, chromosome X and chromosome Y for the sex chromosome aneuploidies.

Apart from digital RCD, the present invention is also useful to enhance the robustness of the other approaches which have been described for the detection of fetal chromosomal aneuploidies from maternal plasma, such as the use of allelic ratios of single nucleotide polymorphisms (SNPs) present on the potentially aneuploid and a reference chromosome (Dhallan, et al. 2007, Lancet, 369, 474-481) and the use of allelic ratios of fetal-specific nucleic acid species, e.g., using fetal-specific methylation signatures (Tong, et al. 2006, Clin Chem, 52, 2194-2202).

Example 5

Size Analysis of Viral Nucleic Acids

The digital sizing technology described in this invention can be used for size analysis of viral nucleic acids. Such size analysis would provide diagnostic and monitoring information for diseases associated with viral infections, including but not limited to cancers associated with viral infections. Examples of the latter include Epstein-Barr virus (EBV) in nasopharyngeal carcinoma (NPC), certain lymphomas (e.g., Hodgkin's lymphoma and NK cell lymphoma), and certain gastric carcinoma; human papillomavirus (HPV) in cervical carcinoma; and hepatitis B virus (HBV) in hepatocellular carcinoma.

Figure 11:
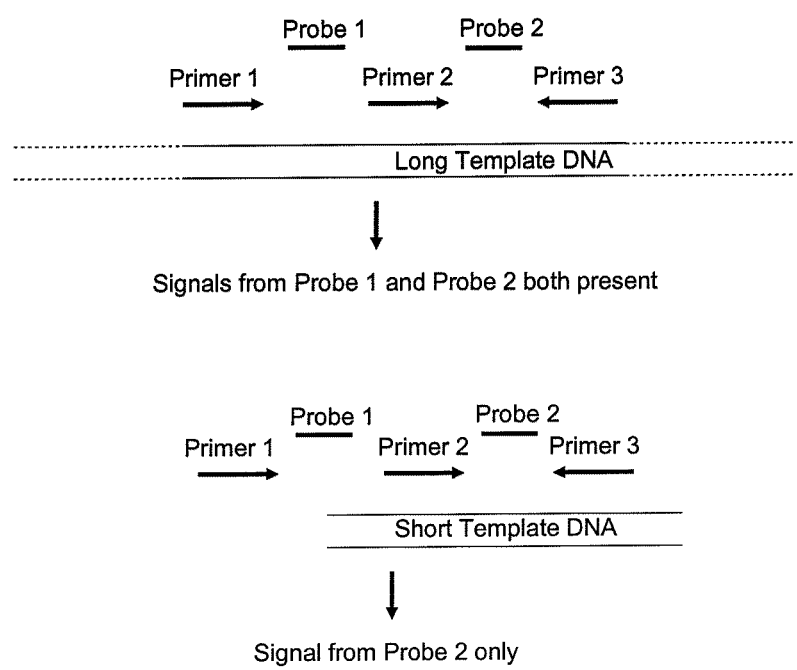

As an example of such an application, the primer and probe configuration illustrated in FIG. 11, is designed to target a sequence within the EBV genome, such as in the BamHI-W fragment, or within the EBNA-1 gene.

When such a system is applied on samples with long EBV DNA, even intact virions, compared with those with short EBV DNA, e.g., plasma from NPC patients, the proportion of long DNA will decrease, while the proportion of short DNA will increase. EBV DNA has been detected in the plasma of some 96% of NPC patients and 7% of individuals without NPC (Lo, et al. 1999, Cancer Res, 59, 1188-1191). The digital sizing system can be used to differentiate EBV DNA in the plasma of NPC patients and those without cancer. As an illustration of how this could be done, a digital sizing system can be developed for EBV DNA. This system can be applied to the plasma of subjects at risk of NPC. Without the digital sizing system, it is expected that some 7% of the subjects will be positive for EBV DNA in the plasma, even if they do not have NPC (Lo, et al. 1999, Cancer Res, 59, 1188-1191). With the digital sizing system, one can establish the relative and absolute concentrations of the long and short EBV DNA fragments in plasma. Reference ranges of the absolute and/or relative concentrations of the long and short EBV DNA fragments in plasma can be determined from a cohort of patients with NPC and in a cohort of range of NPC subjects would be regarded as high risk for having NPC. Conversely, those with values within the range of normal subjects would be regarded as low risk for having NPC. The use of the digital sizing system would be expected to reduce the cost of having to investigate the latter group of subjects with additional investigative procedures, e.g., nasopharyngeal endoscopy. This system would also be useful for the other cancers associated with EBV, e.g., certain lymphomas (Lei, et al., 2002, Clin Cancer Res 8:29-34 and Lei et al., 2000, Br J Haematol 111:239-246).

Example 6

Size Analysis of Nucleic Acids Containing Tumor-Associated Molecular Alterations A number of molecular alterations are associated with the neoplastic process, including oncogene mutations (e.g., KRAS mutations) (Anker, et al. 1997, Gastroenterology, 112, 1114-1120), oncogene amplification (e.g., erbB-2 amplifications) (Chiang, et al. 1999, Clin Cancer Res, 5, 1381-1386) and promoter hypermethylation of tumor suppressor genes (e.g., p16 and RASSF1A hypermethylation) (Baylin, et al. 2001, Hum Mol Genet, 10, 687-692; Hesson, et al. 2007, Dis Markers, 23, 73-87; Wong, et al. 1999, Cancer Res, 59, 71-73). Of particular relevance to cancer detection and monitoring, many of such changes have also been observed in the body fluids of cancer patients, including blood (including its various components, including plasma and serum), urine, saliva, peritoneal fluid, etc. Many of these fluids contain a mixture of neoplastic and non-neoplastic nucleic acids. These two categories of nucleic acids will be expected to have different sizes. Furthermore, cancer patients also have a different overall size distribution of DNA in certain bodily fluids such as plasma, when compared with individuals without cancer (Jiang, et al. 2006, Int J Cancer, 119, 2673-2676).

Thus, the digital sizing technology described herein can also be used to detect, monitor, and prognosticate cancer patients.

Figure 12:
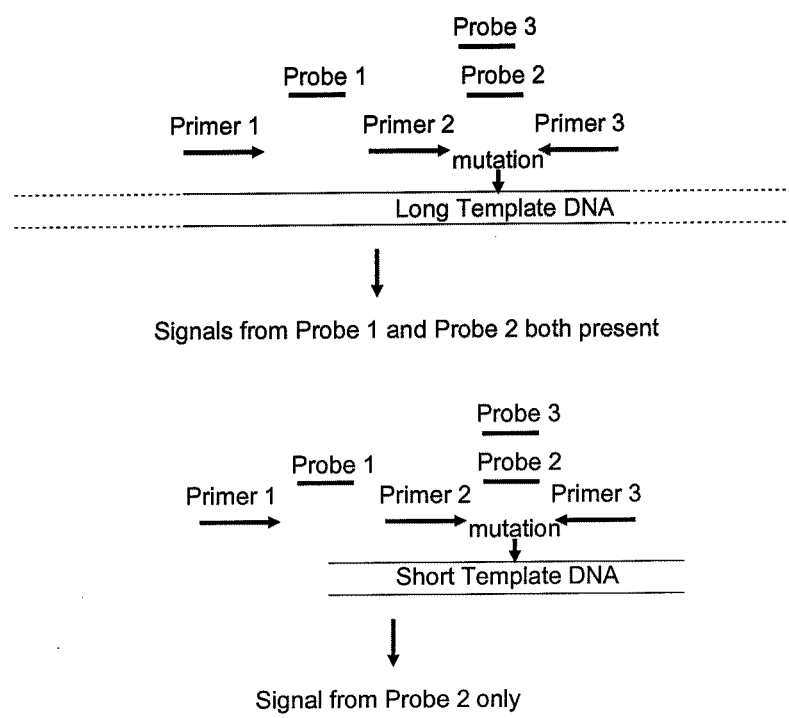

As an illustration of the application of this technology, the example shown in FIG. 12 is constructed. In this example, a mutation in an oncogene, e.g., KRAS, is to be detected.

The primer and probe sequences are constructed towards the KRAS gene. Probe 2 and Probe 3 are designed in such a way that they can differentiate the presence of a mutation (Probe 2) or wild-type (Probe 3) sequence of the KRAS gene. Probe 1, Probe 2 and Probe 3 are labeled with different fluorescence reporters. Thus, following digital PCR analysis, a significant proportion of wells will not contain any signals. For those with the probe signals, any well with the signal from Probe 1 will signify the presence of long template DNA. This Probe 1 signal will be accompanied by a signal from either Probe 2 (if a mutant template is present) or Probe 3 (if a wild-type template is present). If there are more than one template molecules within a well, then it is possible for both Probe 2 and Probe 3 signals to be present concurrently. If the signal from Probe 1 is not present, then it indicates the presence of a short template molecule in that well. In such a well, the presence of Probe 2 or Probe 3 signal will indicate the presence of a short mutant or a short wild-type template, respectively.

This system can also be performed using primer extension followed by mass spectrometry. In such a system, Probe 1 will be replaced by Extension Primer 1; Probe 2 and Probe 3 can be replaced by a single Extension Primer 2. Extension Primer 2 can be designed to terminate one base 5' of the mutation and such that the extension products from the mutant and wild-type templates are distinguishable by molecular masses.

It is also possible that the system can be constructed such that the detection of the long template is done by a fluorescence probe while the differentiation of the mutant and wild-type templates is performed by primer extension followed by mass spectrometry. Those of skilled in the art should be able to construct variants along the core invention described here.

In the context of detecting oncogene amplification in bodily fluids, the digital sizing technology can be used to identify a size window at which the tumor-associated oncogene amplification is most readily observed.

Example 7

Focused Analysis of Short Nucleic Acid Fragments by Digital PCR-Based Size Analysis Methods:

By designing PCR primers specifying amplicons of certain combination of lengths, selective analysis of a subpopulation of nucleic acid molecules of a predetermined size window, amongst a larger population of nucleic acid molecules, could be achieved. This was exemplified by showing the selective enrichment of fetal DNA in maternal plasma. Circulating fetal DNA in maternal plasma was previously reported to be of a shorter length than DNA molecules of maternal origin (Chan et al., 2004 *Clin Chem,* 50, 88-92). In order to achieve a selective discrimination of short fetal DNA molecules among the long maternal DNA molecules in maternal plasma, various PCR amplicon sizes for detecting either the long or the short DNA templates in maternal plasma were investigated. Maternal plasma was collected from pregnant women carrying male fetuses. Six PCR assays specifying amplicon sizes ranging from 213 by to 51 by were designed towards ZFX and ZFY gene regions. The ZFX target, on the X chromosome, was present in both the maternal and fetal genomes. The ZFY target, on the Y chromosome, was only present in the fetal genome. The amplicon lengths and the sequences of PCR and extension primers are shown in the table below.

|  | ZFXY assays | | | | | |
|---|---|---|---|---|---|---|
|  | 213_51[a] | 213_82 | 213_64 | 179_64 | 179_51 | 149_60 |
| Forward PCR primer: | | | | | | |
| Long amplicon | F-213 bp[b] | F-213 bp | F-213 bp | F-179 bp | F-179 bp | F-149 bp |
| Short amplicon | F-51 bp | F-82 bp | F-64 bp | F-64 bp | F-51 bp | F-60 bp |
| Reverse PCR primer | R-a | R-a | R-a | R-a | R-a | R-b |
| Extension primer: | | | | | | |
| Long amplicon | L-a | L-a | L-a | L-b | L-b | L-c |
| Short amplicon | S-a | S-a | S-a | S-a | S-a | S-b |

[a] the assays were named in a way that the former and the latter numbers separated by the underscore indicate the amplicon sizes of the long and short PCR assays, respectively, in the multiplex assay
[b] the primer sequences are shown below (SEQ ID NOS: 14-27):

| Primer | Sequence |
|---|---|
| F-213 bp | ACGTTGGATGAACTGTGCATAACTTTGTTCCTGA |
| F-179 bp | ACGTTGGATGTCAGTTGTAATCCAAGATGTT |
| F-149 bp | ACGTTGGATGTTTAAGGAGCTGATG |
| F-82 bp | ACGTTGGATGTCATTCCTGAGCAAGTGCTG |
| F-64 bp | ACGTTGGATGTGGACTCAGATGTAACTGAAGA |
| F-60 bp | ACGTTGGATGGACATAACTGTGCATAA |
| F-51 bp | ACGTTGGATGAACTGAAGAAGTTTCTTTA |
| R-a | ACGTTGGATGGCTAAAACATCATCTGGGAC |
| R-b | ACGTTGGATGAACATCTTGGATTACAACTGA |
| L-a | AACATCTTGGATTACAACTG |
| L-b | CATCATTCCTGAGCAAGTG |
| L-c | CACACATGGATGGTGATC |
| S-a | TCATCTGGGACTGTGCA |
| S-b | GTTCCTGATGACCCAGA |

Digital PCRs were performed in a 384-well format. Primer extension assays were carried out and the size-specific extension products were determined in a mass spectrometry system (Sequenom) as described in Example 1. The sizes of the detected DNA molecules were determined by the detection of the relevant size-specific extension products. The ZFX or ZFY genes would give extension products of different masses using the short extension primers, S-a or S-b. The identification of the gene fragment as being ZFX or ZFY was based on detecting the relevant extension product within the short amplicon.

Results

Figure 13A:
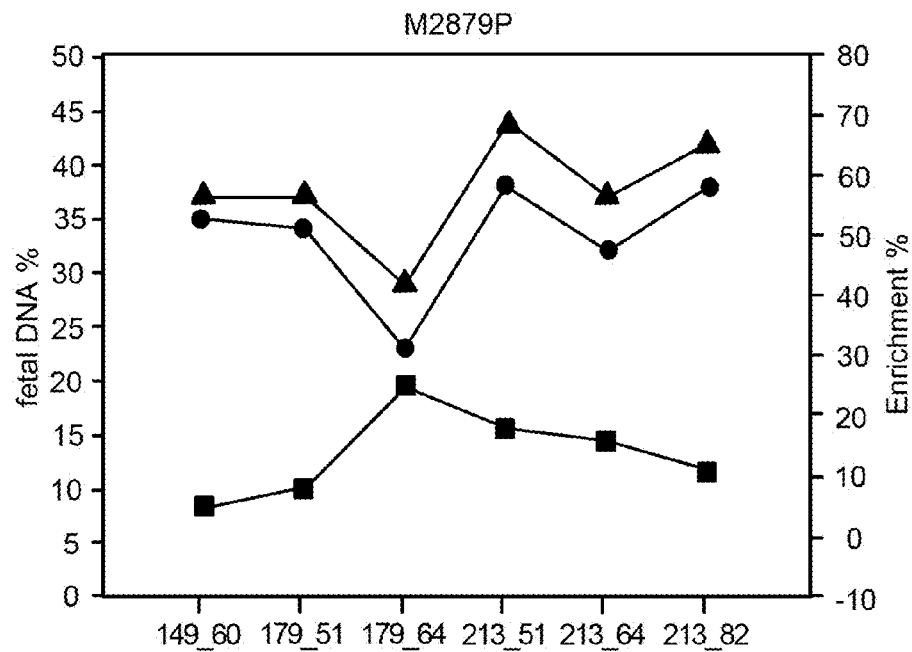
FIGS. 13a-13d: Fetal percentages in third trimester maternal plasma calculated using assays of different size combinations. Panels a, b, and c show results for individual third trimester maternal plasma samples. Panel d shows the averaged results from the three maternal plasma samples.
Figure 13B:
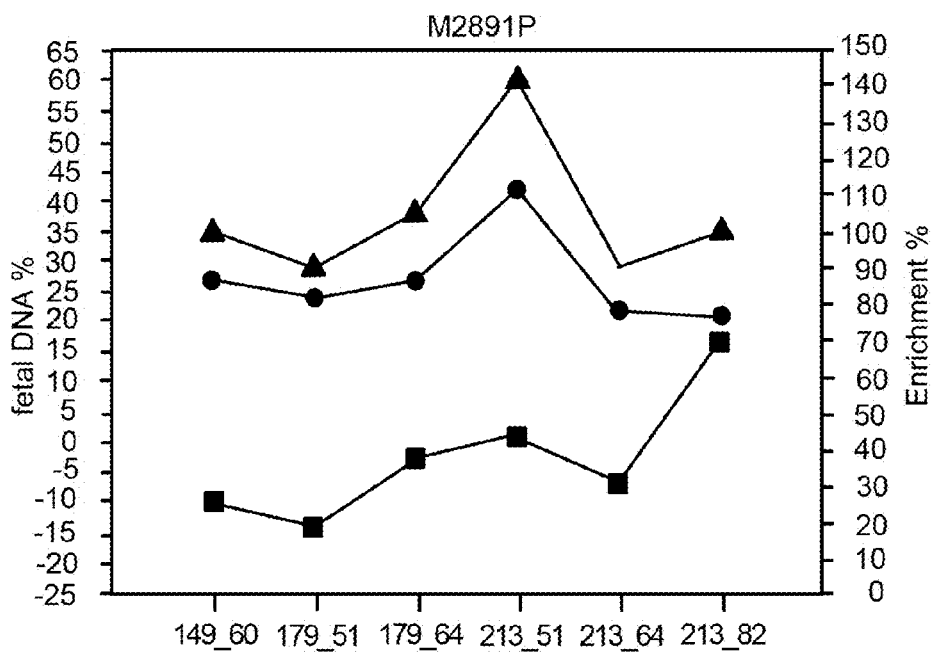
Figure 13C:
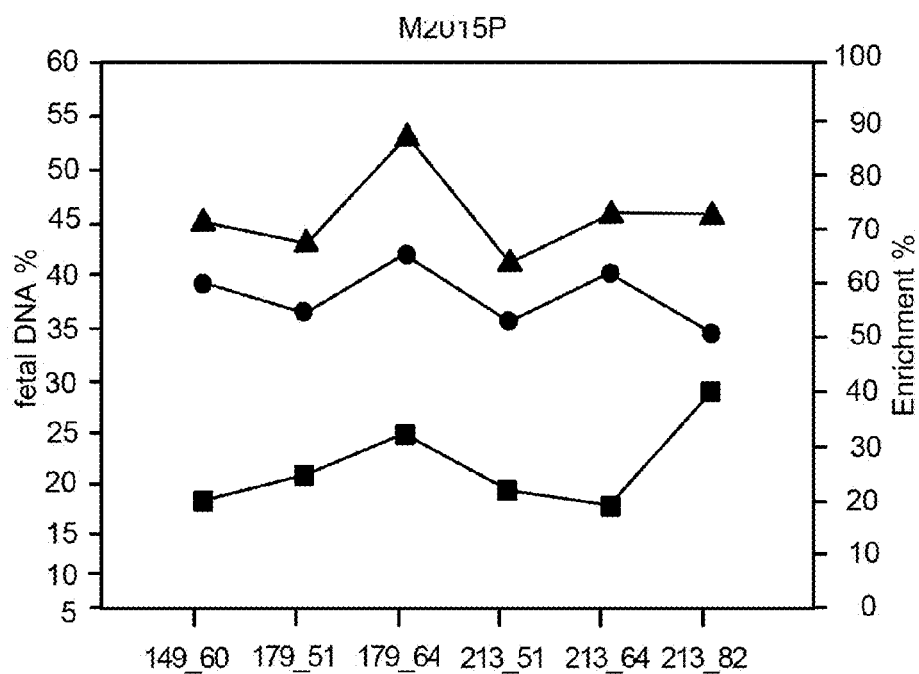
Figure 13D:
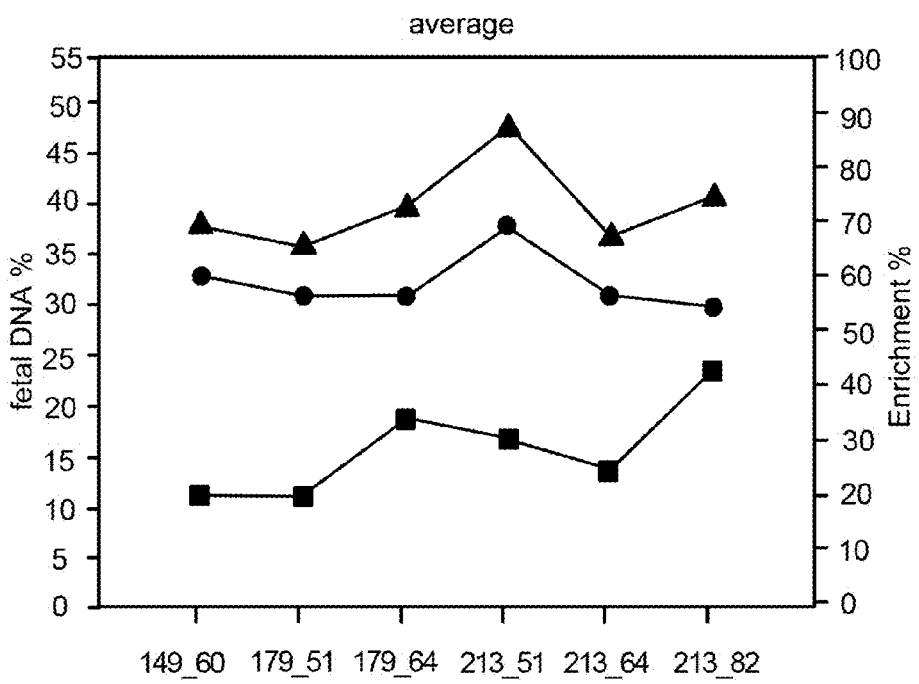

In the first part of the study, six PCR assays with combinations of short and long amplicons of different sizes were studied in three third trimester maternal plasma samples. Fetal DNA percentages were calculated using two approaches as described in Example 1. The percentages were first calculated using wells containing the X- and Y-specific signals, without considering the sizes. The percentages were then re-calculated using the wells showing signals of the short DNA amplicons only. As shown in FIG. 13, the calculated fractional fetal DNA concentrations were higher by using only the short DNA molecules, compared with those calculated using both the long and short molecules. The increments in the fractional fetal DNA concentrations achieved or percentage enrichment were further calculated. FIG. 13d shows the result averaged from the three plasma samples. Assays 179_64 and 213_82 shows the greatest increments by this size analysis strategy while assay 213_51 shows the highest fetal percentage among the six assays evaluated in this example. Thus, these three assays were selected for further study in maternal plasma samples from an earlier gestational age.

Figure 14A:
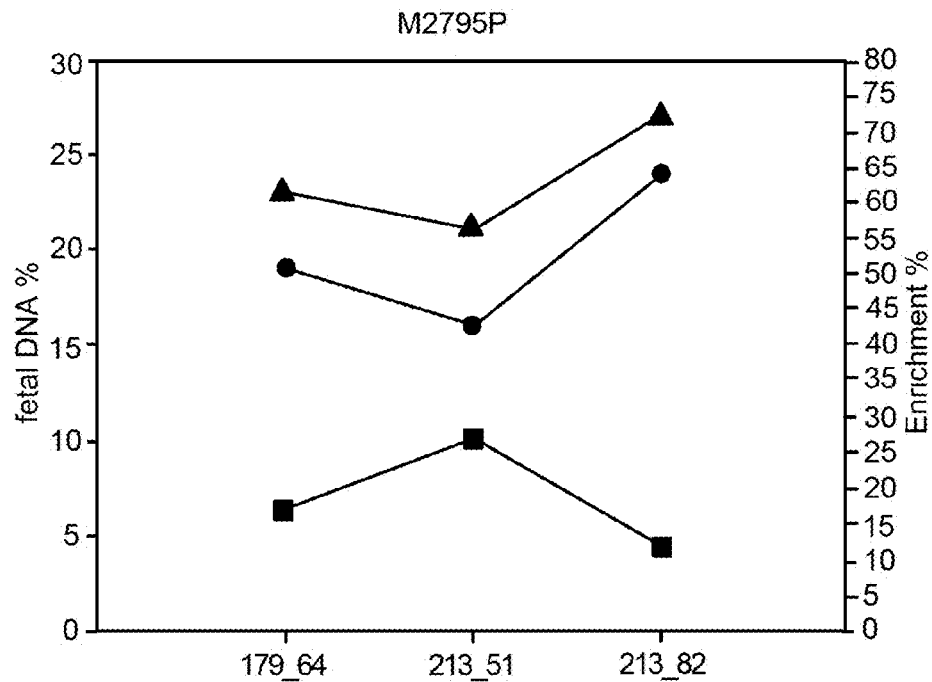
FIGS. 14a-14d: Fetal percentages in first trimester maternal plasma calculated using assays of different size combinations. Panels a, b, c, and d show results for individual third trimester maternal plasma samples. Panel e shows the averaged results from the three maternal plasma samples.
Figure 14B:
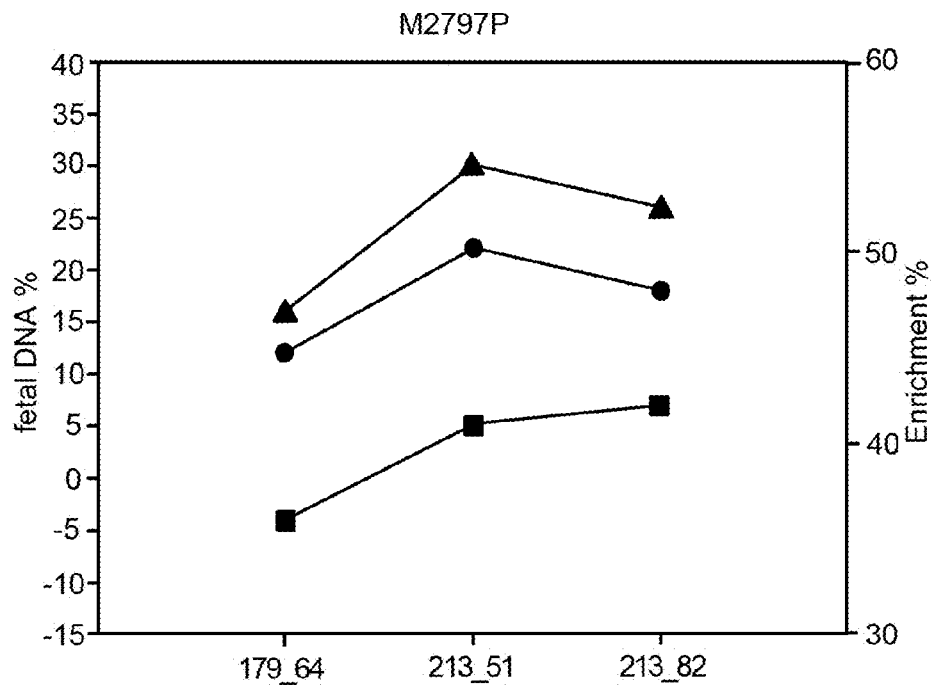
Figure 14C:
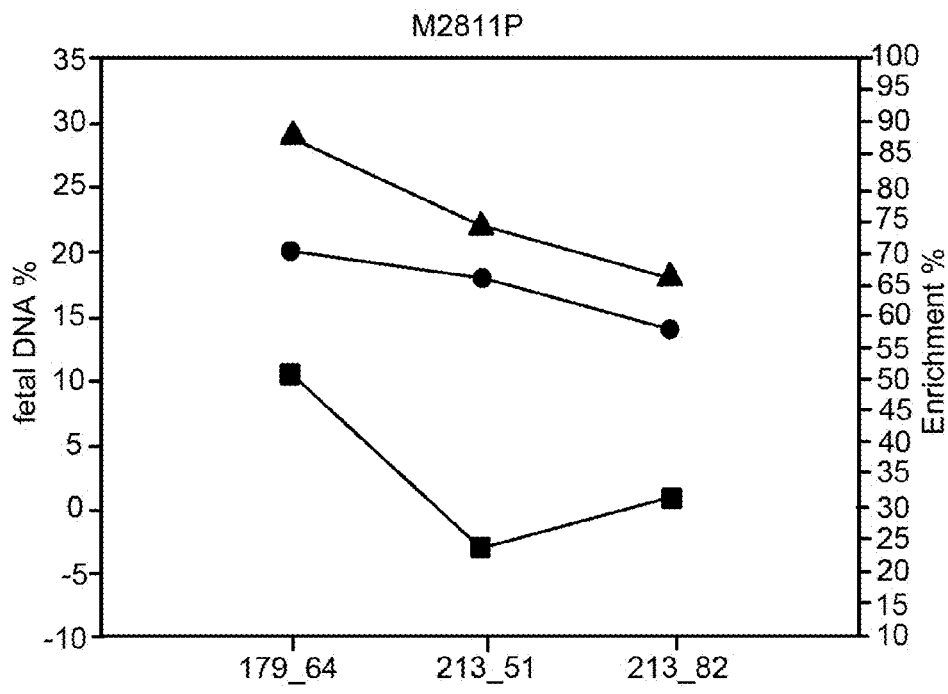
Figure 14D:
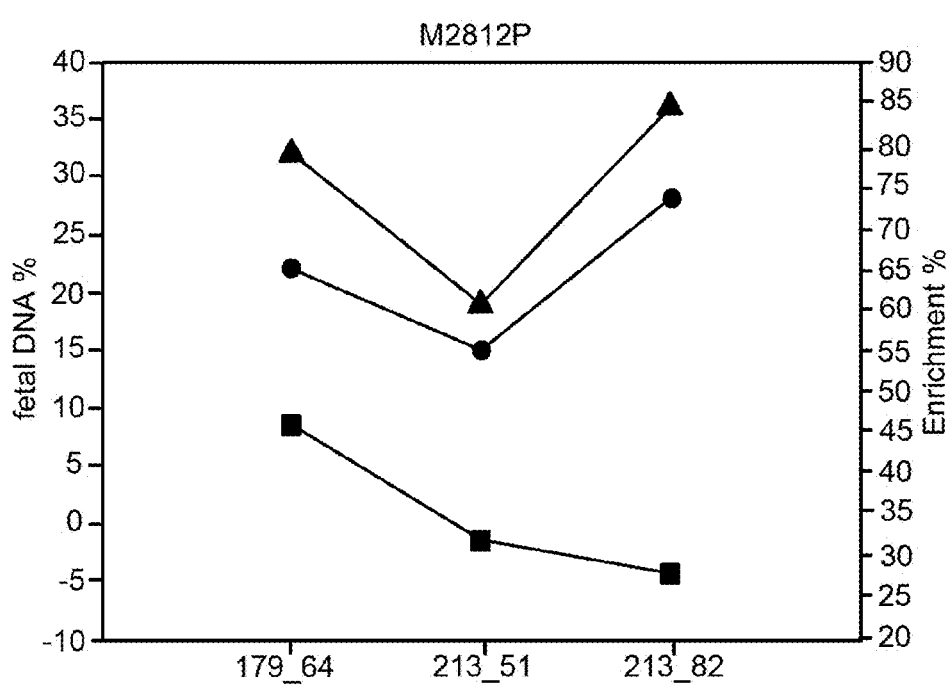
Figure 14E:
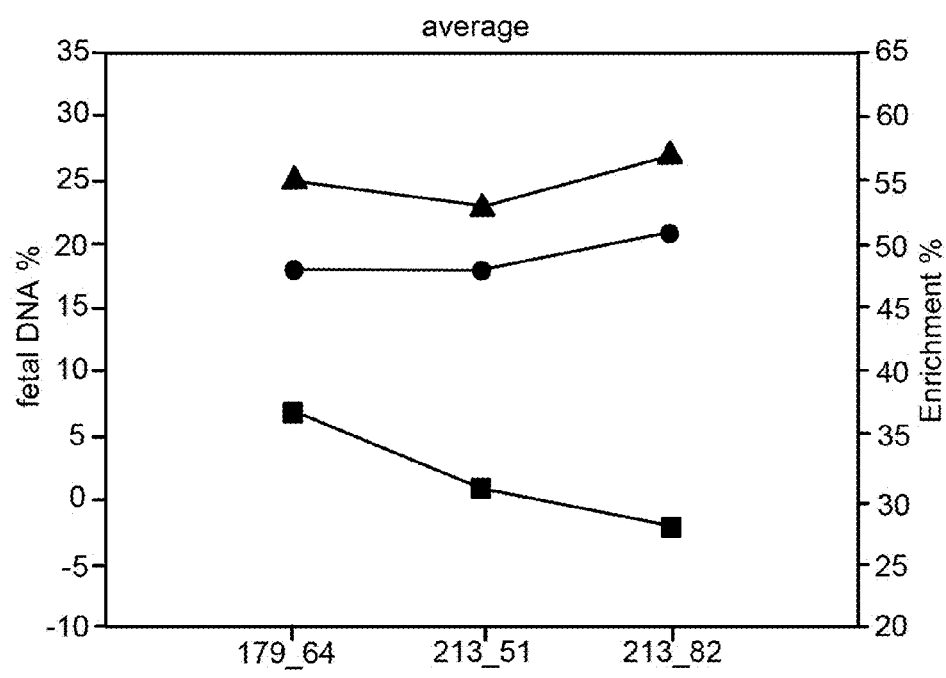

In the second part of the study, assays 179_64, 213_51 and 213_82 were studied in four first trimester maternal plasma samples. The fractional fetal DNA concentrations and the percentage enrichment by this size analysis strategy are shown in FIG. 14. As shown in FIG. 14e which shows data averaged from the four maternal plasma samples, assay 179_64 shows the highest percentage enrichment. The result demonstrates that the combination of 179 bp and 64 bp amplicons shows the greatest power to discriminate between maternal and fetal molecules in maternal plasma and thus resulted in the highest degree of fetal DNA enrichment.

In the third part of the study, the assay 179_64 was further investigated in a total of ten first trimester maternal plasma samples. The result is tabulated below. By using the sizing strategy, the calculated fractional fetal DNA concentrations increased by an average of 36%.

Example 8

DNA Size Analysis for Fetal Single Nucleotide Polymorphism in Maternal Plasma

Methods

The size analysis strategy for maternal plasma fetal DNA quantification was further adopted for fetal SNP detection in maternal plasma. A polymorphic SNP (rs8130833) on PLAC4 was utilized to differentiate fetal and maternal-derived DNA molecules. Duplex PCR assay with amplicon sizes of 179 bp and 63 by was designed. The PLAC4 SNP was amplified by the 63 bp-assay. The sequences of the primers are tabulated below (SEQ ID NOS:28-32):

Forward PCR Primer (5' to 3'):

```
Long amplicon      ACGTTGGATGGCCTGGAAGTAACGTGATCC
Short amplicon     ACGTTGGATGTAGAACCATGTTTAGGCCAG
```

Reverse PCR Primer (5' to 3'):

```
                   ACGTTGGATGGCAACACCATTTGGGTTAAAT
```

Extension Primer (5' to 3'):

```
Long amplicon      AGTATAGAGCCATAAAAGCC
Short amplicon     AGGCCAGATATATTCGTC
```

First trimester plasma samples were collected from 10 pregnant women. These women had different genotypes for the SNP than the fetuses that they were carrying. Digital PCR were performed in a 384-well format. Primer extension assays were then carried out and the extension products generated from the short or long amplicons were determined using mass spectrometry (Sequenom) as described in Example 1. The SNP alleles were discriminated based on the masses of the extension products of the short amplicon.

Results

The results are tabulated below. The fractional concentrations of the fetal specific SNP allele were increased by an average of 31% by using only the wells containing signals of the short amplicons when compared with those calculated from wells containing signals of both the short and long DNA fragments.

|         | digital PCR data | | | | | | | | | fetal % | | |
|---------|------|-----|---|-----|----|----|----|----|-----|------------------|---------------------|-------------|
| samples | wells | neg | L | X   | Y  | LX | LY | XY | LXY | all fragements   | short fragments     | enrichment* |
| M2790P  | 380  | 109 | 0 | 163 | 17 | 65 | 1  | 13 | 12  | 19.8             | 31.7                | 60.5        |
| M2791P  | 384  | 159 | 0 | 151 | 15 | 31 | 2  | 17 | 9   | 26.4             | 32.8                | 24.2        |
| M2795P  | 383  | 269 | 0 | 82  | 8  | 19 | 1  | 2  | 2   | 19.5             | 22.8                | 17.1        |
| M2797P  | 377  | 206 | 0 | 114 | 6  | 44 | 1  | 5  | 1   | 11.6             | 15.7                | 35.7        |
| M2811P  | 384  | 256 | 0 | 77  | 10 | 36 | 0  | 2  | 3   | 19.6             | 29.5                | 50.6        |
| M2812P  | 383  | 268 | 0 | 68  | 8  | 32 | 0  | 5  | 2   | 21.7             | 31.8                | 46.2        |
| M3616P  | 384  | 268 | 0 | 86  | 5  | 24 | 1  | 0  | 0   | 8.9              | 9.8                 | 10.3        |
| M3591P  | 383  | 288 | 0 | 74  | 7  | 12 | 0  | 2  | 0   | 16.7             | 19.4                | 16.3        |
| M3593P  | 384  | 297 | 0 | 50  | 6  | 30 | 0  | 1  | 0   | 14.4             | 22.9                | 58.7        |
| M3501P  | 384  | 269 | 0 | 75  | 6  | 30 | 0  | 4  | 0   | 14.6             | 20.6                | 40.3        |

$$*\text{enrichment \%} = \frac{(\text{fetal \% calculated from short fragments} - \text{fetal \% calculate from all fragments})}{\text{fetal \% calculated from all fragments}} \times 100\%$$

|  | genotype | | digital PCR data | | | | | | | | | fetal % | | |
|---|---|---|---|---|---|---|---|---|---|---|---|---|---|---|
| samples | fetus | mother | wells | neg | L | A | G | LA | LG | AG | LAG | all fragments | short fragments | enrichment |
| M2304P | AG | A | 383 | 279 | 0 | 62 | 18 | 17 | 2 | 4 | 1 | 43 | 49 | 15 |
| M2761P | AG | A | 384 | 283 | 0 | 64 | 2 | 33 | 1 | 1 | 0 | 7 | 8 | 18 |
| M2329P | AG | A | 384 | 265 | 0 | 76 | 6 | 30 | 1 | 4 | 2 | 18 | 24 | 32 |
| M2325P | AG | A | 384 | 246 | 0 | 103 | 4 | 27 | 0 | 2 | 2 | 9 | 12 | 32 |
| M1897P | AG | A | 380 | 290 | 0 | 58 | 1 | 31 | 0 | 0 | 0 | 2 | 3 | 60 |
| M1853P | AG | A | 384 | 263 | 0 | 80 | 4 | 34 | 1 | 1 | 1 | 10 | 12 | 28 |
| M1854P | AG | G | 382 | 239 | 0 | 5 | 88 | 2 | 43 | 2 | 3 | 14 | 18 | 33 |

This approach can also be used if the fetal SNP is a pathogenic mutation, such as that in the β-globin gene causing β-thalassemia, sickle cell anemia or hemoglobin E disease; or that in the cystic fibrosis transmembrane conductance regulator gene causing cystic fibrosis.

All patents, patent applications, and other publications cited in this application, including published amino acid or polynucleotide sequences, are incorporated by reference in the entirety for all purposes.

What is claimed is:

1. A method for determining in a sample taken from a woman pregnant with a fetus the relative amount of a target gene derived from the woman and from the fetus, comprising the steps of:
   (i) preparing multiple equal fractions from the sample, wherein more than 50% of the fractions contain no more than 1 target gene molecule per fraction;
   (ii) treating each fraction with a methylation-sensitive restriction enzyme, which cleaves the target gene at a predetermined location when there is no methylation at the location and does not cleave the target gene at the location when there is methylation at the location;
   (iii) performing amplification reactions in each fraction using at least one forward primer with at least two reverse primers, or using at least two forward primers with at least one reverse primer, wherein the predetermined location is between at least one pair of the forward and reverse primers but is not between at least one, different, pair of forward and reverse primers;
   (iv) detecting in each fraction amplified nucleotide sequence from each pair of forward and reverse primers; and
   (v) counting the number of fractions in which different combinations of amplified nucleotide sequences from different pairs of forward and reverse primers are detected, thereby determining the relative amount of the target gene derived from the woman and the fetus in the sample.

2. The method of claim 1, wherein the target gene derived from the woman is hypermethylated at the predetermined location and the target gene derived from the fetus is hypomethylated at the predetermined location.

3. The method of claim 2, wherein the target gene is SERPINB5.

4. The method of claim 1, wherein the target gene derived from the woman is hypomethylated at the predetermined location and the target gene derived from the fetus is hypennethylated at the predetermined location.

5. The method of claim 4, wherein the target gene is RASSF1A.

6. The method of claim 1, wherein the blood sample is blood, plasma, or serum.

7. The method of claim 1, wherein the multiple equal fractions are multiple equal dilutions from the sample.

8. The method of claim 1, wherein step (i) is performed by a microfluidics system.

9. The method of claim 1, wherein the amplification reactions are polymerase chain reactions (PCR).

10. The method of claim 9, wherein the PCR is real-time PCR.

11. The method of claim 9, wherein a fluorescent dye is present in the PCR.

12. The method of claim 11, wherein the fluorescent dye is SYBR Green or LC Green.

13. The method of claim 1, wherein the amplified nucleotide sequences from different pairs of forward and reverse primers are of distinct lengths.

14. The method of claim 1, wherein step (iii) is performed by emulsion polymerase chain reaction.

15. The method of claim 1, wherein step (iv) is performed by melting curve analysis.

16. The method of claim 1, wherein step (iv) is performed by electrophoresis.

17. The method of claim 1, wherein step (iv) is performed by sequence-specific hybridization with probes with detectable labels, wherein each probe has a distinct detectable label and specifically hybridizes with an amplified nucleotide sequence from a pair of forward and reverse primers.

18. The method of claim 17, wherein the detectable labels are distinct fluorescent molecules.

19. The method of claim 1, wherein step (iv) is performed by primer extension reactions or by sequencing reactions.

20. The method of claim 19, wherein products of the primer extension reactions are detected by mass spectrometry.

21. The method of claim 1, wherein step (iv) is performed by flow cytometry.

22. The method of claim 1, wherein steps (iii) and (iv) are performed by BEAMing.

23. The method of claim 1, wherein the amplification reactions in step (iii) are performed consecutively using different pairs of forward and reverse primers.

24. The method of claim 1, wherein the amplification reactions in step (iii) are performed concurrently using different pairs of forward and reverse primers.

* * * * *